(12) United States Patent
Solem

(10) Patent No.: US 8,696,696 B2
(45) Date of Patent: Apr. 15, 2014

(54) DEVICE AND KIT FOR TREATMENT OF DISORDERS IN THE HEART RHYTHM REGULATION SYSTEM

(71) Applicant: Syntach AG, Schaffhausen (CH)

(72) Inventor: Jan Otto Solem, Bjärred (SE)

(73) Assignee: Syntach AG, Schaffhausen (CH)

( * ) Notice: Subject to any disclaimer, the term of this patent is extended or adjusted under 35 U.S.C. 154(b) by 0 days.

(21) Appl. No.: 13/764,681

(22) Filed: Feb. 11, 2013

(65) Prior Publication Data

US 2013/0226070 A1   Aug. 29, 2013

Related U.S. Application Data

(63) Continuation of application No. 11/910,524, filed as application No. PCT/EP2005/005363 on May 17, 2005, now abandoned.

(51) Int. Cl.
*A61B 17/32* (2006.01)

(52) U.S. Cl.
USPC .................................................. 606/170

(58) Field of Classification Search
USPC ......... 606/159, 167, 170; 623/1.1, 1.11, 1.14, 623/1.15, 1.16, 1.2, 1.3, 1.31, 1.36
See application file for complete search history.

(56) References Cited

U.S. PATENT DOCUMENTS

| | | | |
|---|---|---|---|
| 7,192,445 B2 | 3/2007 | Ellingsen et al. | |
| 2003/0055491 A1 | 3/2003 | Schwartz et al. | |
| 2003/0065307 A1* | 4/2003 | Lesh | 604/509 |
| 2003/0065382 A1 | 4/2003 | Fischell et al. | |
| 2004/0215310 A1 | 10/2004 | Amirana | |
| 2004/0243107 A1 | 12/2004 | Macoviak et al. | |
| 2004/0249443 A1 | 12/2004 | Shanley et al. | |
| 2005/0015129 A1 | 1/2005 | Mische | |
| 2005/0131503 A1 | 6/2005 | Solem | |
| 2009/0163941 A1 | 6/2009 | Solem et al. | |
| 2009/0264983 A1 | 10/2009 | Solem | |

FOREIGN PATENT DOCUMENTS

| | | |
|---|---|---|
| WO | WO 03/003948 A1 | 1/2003 |
| WO | WO 2004/078065 A2 | 9/2004 |

OTHER PUBLICATIONS

WIPO, European International Preliminary Examining Authority, International Preliminary Report on Patentability mailed Sep. 25, 2007 in International Patent Application No. PCT/EP2005/005363, 15 pages.
United States Patent and Trademark Office, Office Action mailed Sep. 6, 2011 in U.S. Appl. No. 11/910,524, 17 pages.
United States Patent and Trademark Office, Final Office Action mailed Apr. 13, 2012 in U.S. Appl. No. 11/910,524, 16 pages.

(Continued)

*Primary Examiner* — Ryan Severson
*Assistant Examiner* — Jonathan W Miles
(74) *Attorney, Agent, or Firm* — Inskeep IP Group, Inc.

(57) ABSTRACT

A tissue cutting device is disclosed, which is structured and arranged to be inserted through the vascular system into a body vessel adjacent to the heart and/or into the heart, and to be subsequently subjected to a change of shape in order to penetrate into the heart tissue. The tissue cutting device may thus be used for treating disorders to the heart rhythm regulation system. A kit of devices provides a plurality of devices for creating a lesion pattern for treating such disorders.

24 Claims, 31 Drawing Sheets

(56) References Cited

OTHER PUBLICATIONS

"Lacerate" as defined by Merriam-Webster, accessed on Mar. 26, 2012; http://www.merriam-webster.com/dictionary/lacerate, 3 pages.

"Incise" as defined by Merriam-Webster, accessed on Mar. 26, 2012; http://www.merriam-webster.com/dictionary/incise, 3 pages.

"Cut" as defined by Merriam-Webster, accessed on Mar. 26, 2012; http://www.merriam-webster.com/dictionary/cut, 7 pages.

* cited by examiner

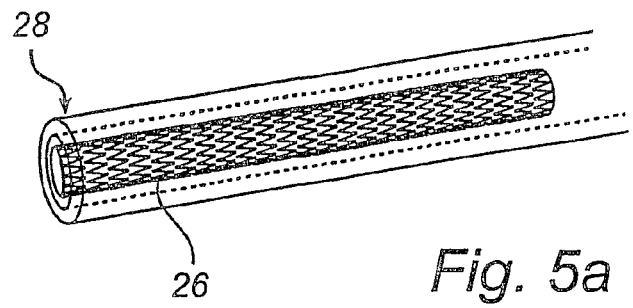
Fig. 5a
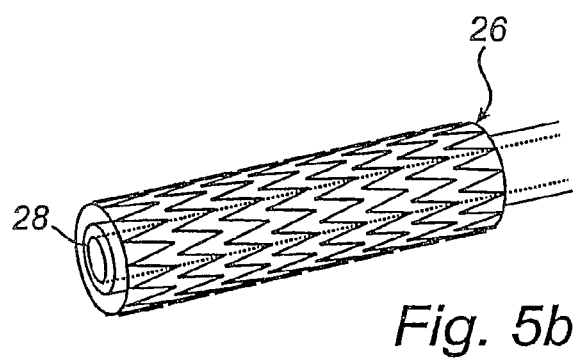
Fig. 5b
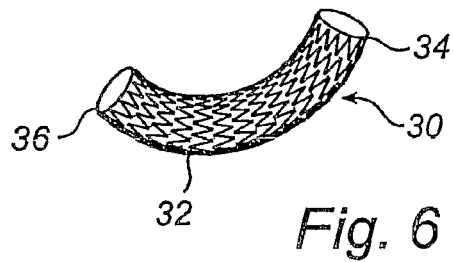
Fig. 6
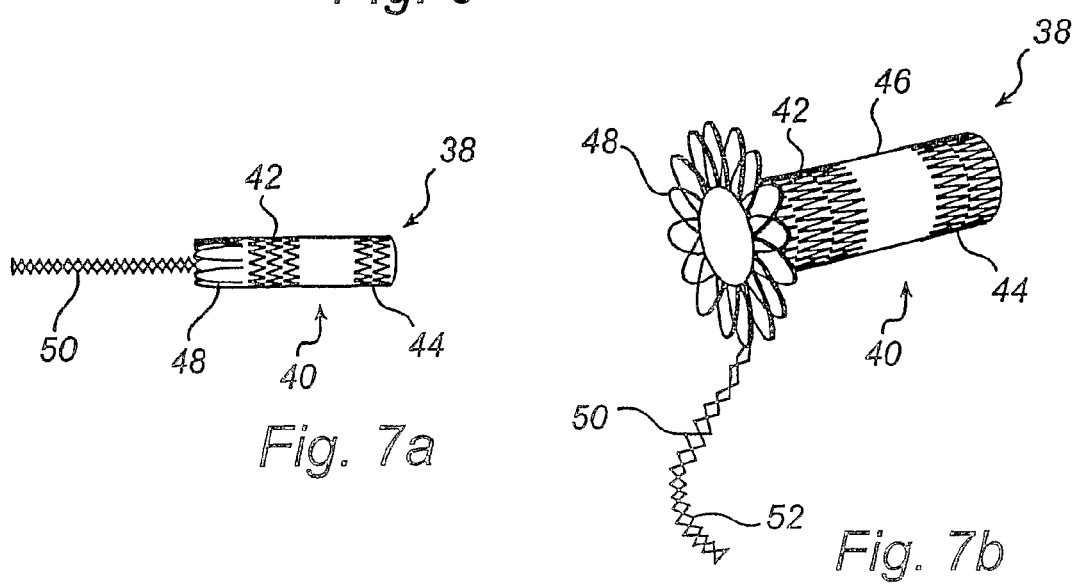
Fig. 7a
Fig. 7b

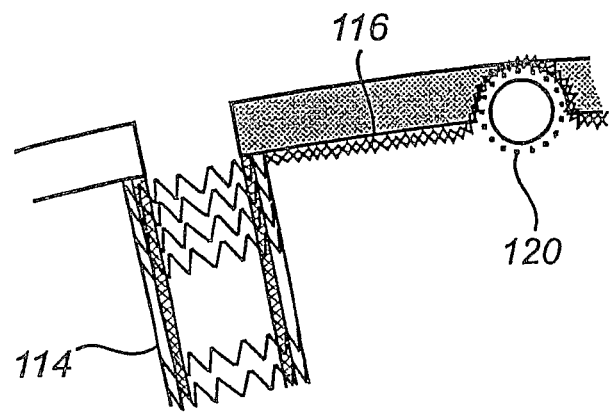
Fig. 17b
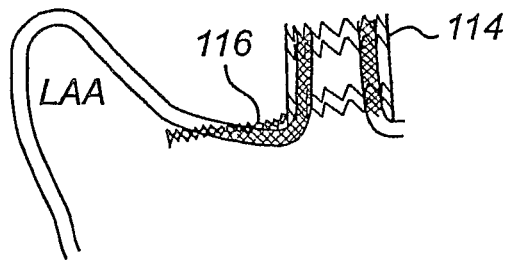
Fig. 17c
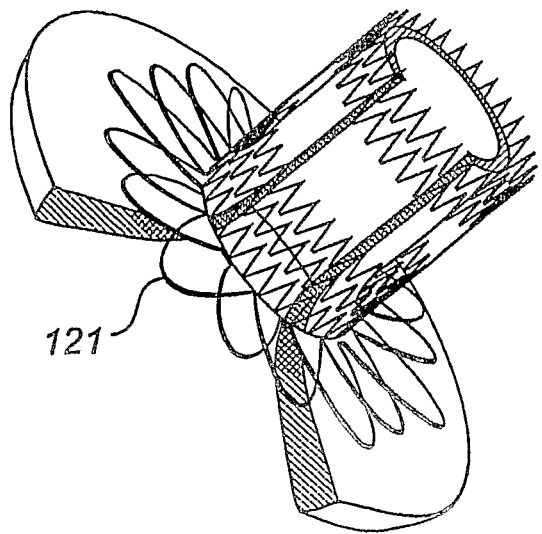
Fig. 17d

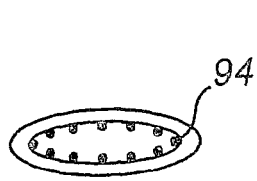
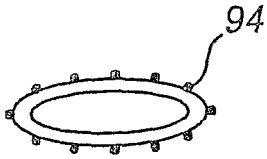
Fig. 26a    Fig. 26b
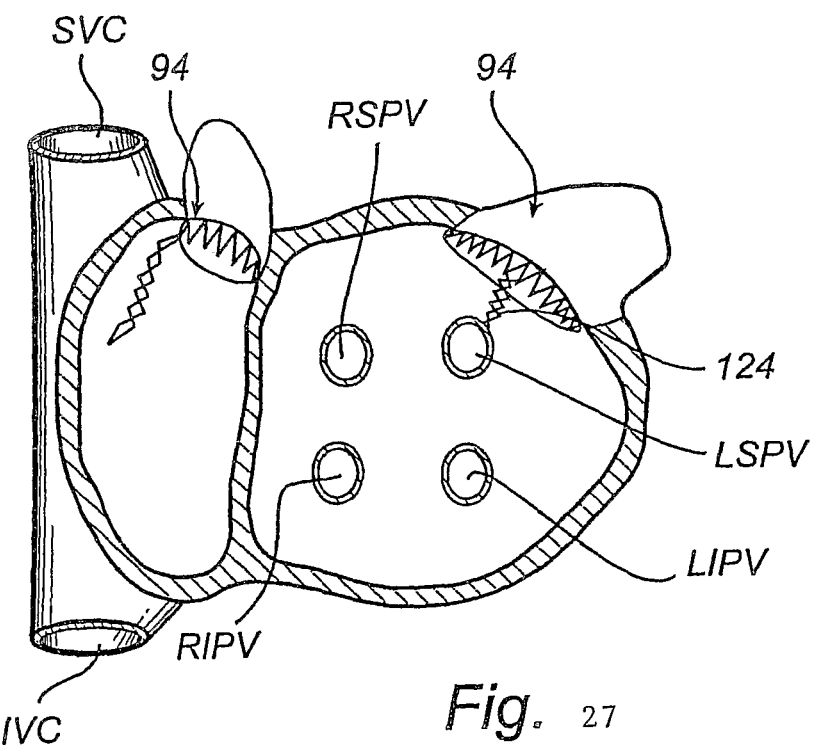
Fig. 27
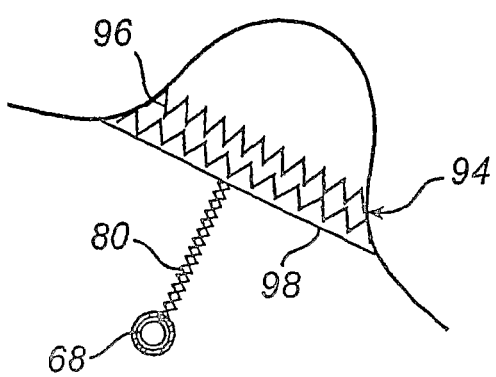
Fig. 28

DEVICE AND KIT FOR TREATMENT OF DISORDERS IN THE HEART RHYTHM REGULATION SYSTEM

RELATED APPLICATIONS

This application is a continuation of U.S. patent application Ser. No. 11/910,524 filed Jul. 22, 2008 entitled A Device And Kit For Treatment Of Disorders In The Heart Rhythm Regulation System, which is the U.S. National Phase of and claims priority to International Application No. PCT/EP2005/005363 filed May 17, 2005 entitled A Device And Kit For Treatment Of Disorders In The Heart Rhythm Regulation System, both of which are hereby incorporated by reference in their entireties.

FIELD OF THE INVENTION

The present invention relates to treatment of disorders the heart rhythm regulation system and, specifically, to a tissue cutting device, a kit of shape-changing devices and a method for treating such disorders.

BACKGROUND OF THE INVENTION

The circulation of blood in the body is controlled by the pumping action of the heart. The heart expands and contracts by the force of the heart muscle under impulses from the heart rhythm regulation system. The heart rhythm regulation system transfers an electrical signal for activating the heart muscle cells.

The normal conduction of electrical impulses through the heart starts in the sinoatrial node, travels across the right atrium, the atrioventricular node, the bundles of His and thereafter spread across the ventricular muscle mass. Eventually when the signal reaches the myocytes specialized in only contraction, the muscle cell will contract and create the pumping function of the heart (see FIG. 1).

The electrical impulses are transferred by specially adapted cells. Such a cell will create and discharge a potential over the cell membrane by pumping ions in and out of the cell. Adjacent cells are joined end-to-end by intercalated disks. These disks are cell membranes with a very low electrical impedance. An activation of a potential in a cell will propagate to adjacent cells thanks to the low impedance of the intercalated disks between the cells. While being at the embryonic stage, all heart muscle cells, the myocytes, have the ability to create and transfer electrical signals. During evolution the myocytes specialize and only those cells necessary for maintaining a stable heart-rate are keeping the ability to create and send electrical impulses. For a more thorough explanation of the propagation of electrical signals in the heart, see e.g. Sandöe, E. and Sigurd, B., *Arrhythmia, Diagnosis and Management, A Clinical Blectrocardiographic Guide*, Fachmed AG, 1984.

The heart function will be impaired if there is a disturbance on the normal conduction of the electrical impulses. Atrial fibrillation (AF) is a condition of electrical disorder in the heart rhythm regulation system. In this condition, premature and fast signals irregularly initiating muscle contractions in the atria as well as in the ventricles will be started in ectopic sites, that is areas outside the sinoatrial node. These signals will be transmitted erratically all over the heart. When more than one such ectopic site starts to transmit, the situation becomes totally chaotic, in contrast to the perfect regularity in a healthy heart, where the rhythm is controlled from the sinoatrial node.

Atrial fibrillation is a very common disorder, thus 5% of all patients that undergo heart surgery suffer from AF. 0.4-2% of a population will suffer from AF, whereas 10% of the population over the age of 65 suffers from AF. 160,000 new cases occur every year in the US and the number of cases at present in the US is estimated to be around 3 million persons. Thus, treatment of atrial fibrillation is an important topic.

Typical sites for ectopic premature signals in AF may be anywhere in the atria, the pulmonary veins (PV), in the coronary sinus (CS), in the superior vena cava (SVC) or in the inferior vena cava (IVC). There are myocardial muscle sleeves present around the orifices and inside the SVC, IVC, CS and the PVs. Especially around the orifice of the left superior pulmonary vein (LSPV) such ectopic sites are frequent, as well as at the orifice of the right superior pulmonary vein (RSPV). In AF multiple small circles of a transmitted electrical signal started in an ectopic site may develop, creating re-entry of the signal in circles and the circle areas will sustain themselves for long time. There may be only one ectopic site sending out signals leading to atrial flutter, or there may be multiple sites of excitation resulting in atrial fibrillation. The conditions may be chronic or continuous since they never stop. In other cases there may be periods of normal regular sinus rhythm between arrhythmias. The condition will then be described as intermittent.

In the chronic or continuous cases, the atrial musculature undergoes an electrical remodelling so that the re-entrant circuits sustain themselves continuously. The patient will feel discomfort by the irregular heart rate, sometimes in form of cannon waves of blood being pushed backwards in the venous system, when the atria contract against a closed arterio-ventricle valve. The irregular action of the atria creates standstill of blood in certain areas of the heart, predominantly in the auricles of the left and right atrium. Here, blood clots may develop. Such blood clots may in the left side of the heart get loose and be taken by the blood stream to the brain, where it creates disastrous damage in form of cerebral stroke. AF is considered to be a major cause of stroke, which is one of the biggest medical problems today.

Today, there are a few methods of treating the problems of disorders to the heart rhythm regulation system. Numerous drugs have been developed to treat AF, but the use of drugs is not effective to a large part of the patients. Thus, there has also been developed a number of surgical therapies.

Surgical therapy was introduced by Drs. Cox, Boineau and others in the late 1980s. The principle for surgical treatment is to cut all the way through the atrial wall by means of knife and scissors and create a total separation of the tissue. Subsequently the tissues are sewn together again to heal by fibrous tissue, which does not have the ability to transmit myocardial electrical signals. A pattern of cutting was created to prohibit the propagation of impulses and thereby isolate the ectopic sites, and thus maintain the heart in sinus rhythm. The rationale for this treatment is understandable from the description above, explaining that there must be a physical contact from myocyte to myocyte for a transfer of information between them. By making a complete division of tissue, a replacement by non-conductive tissue will prohibit further ectopic sites to take over the stimulation. The ectopic sites will thus be isolated and the impulses started in the ectopic sites will therefore not propagate to other parts of the heart.

It is necessary to literally cut the atria and the SVC and the IVC in strips. When the strips are sewn together they will give the impression of a labyrinth guiding the impulse from the sinoatrial node to the atrioventricular node, and the operation was consequently given the name Maze. The cutting pattern is illustrated in FIG. 2 and was originally presented in J L Cox, T E Canavan, R B Schuessler, M E Cain, B D Lindsay, C Stone, P K Smith, P B Corr, and J P Boineau, *The surgical treatment of atrial fibrillation. Intraoperative electrophysiologic mapping and description of the electrophysiologic basis of atrial flutter and atrial fibrillation*, J Thorac Cardiovasc Surg, 1991 101:406-426. The operation has a long-time success of curing patients from AF in 90% of the patients. However, the Maze operation implicate that many suture lines have to be made and requires that the cuts are completely sealed, which is a demanding task for every surgeon that tries the method. The operation is time consuming, especially the time when the patients own circulation has to be stopped and replaced by extracorporeal circulation by means of a heart-lung machine. Thus mortality has been high and the really good results remained in the hands of a few very trained and gifted surgeons.

The original Maze operation has therefore been simplified by eliminating the number of incisions to a minimum, still resulting in a good result in most cases. The currently most commonly used pattern of incisions is called Maze III (see FIG. 3).

Other methods of isolating the ectopic sites have also been developed recently. In these methods, the actual cutting and sewing of tissue has been replaced by methods for killing myocyte cells. Thus, one may avoid separating the tissue, instead one destroy the tissue by means of heat or cooling in the Maze pattern to create a lesion through the heart wall. The damaged myocyte tissue can not transfer signals any more and therefore the same result may be achieved. Still the chest has to be opened, and the heart stopped and opened. Further, the energy source has to be carefully controlled to affect only tissue that is to be destroyed.

A large number of devices have now been developed using various energy sources for destroying the myocyte tissue. Such devices may use high radio frequency energy, as disclosed in e.g. U.S. Pat. No. 5,938,660, or microwaves, ultrasound or laser energy. Recently, devices have been developed for catheter-based delivery of high radio frequency energy through the venous and or arterial systems. However, this has so far had limited success due to difficulties in navigation and application of energy and also late PV stenosis has been reported. Further, devices using cooling of tissue has used expanding argon gas or helium gas to create temperatures of −160° C. Using an instrument with a tip, tissue can be frozen and destroyed.

WO03/003948 discloses an apparatus for treating, preventing, and terminating arrhythmias. The device, which is implanted and left at the target site, is provided with protrusions that pierce the tissue, via self-expansion or balloon expansion, to gain access to the cells of said target site. The protrusions are used to conduct drugs to the cells, which drugs may cause cell death to thereby induce cellular changes that may lead to treatment of arrhythmias. Nowhere in WO03/003948 is a device described that by expansion fully penetrates the wall of the blood vessel to disrupt cardiac impulses, which device then is bio-absorbed and thereby eliminated from the target site. The device according to WO03/003948 is not a cutting device.

OBJECTS AND SUMMARY OF THE INVENTION

Accordingly, the present invention seeks to mitigate, alleviate or eliminate one or more of the above-identified deficiencies and to provide a new device, and kit of devices, suitable for a method for treatment of disorders to the heart rhythm regulation system of the kinds referred to, according to the appended independent claims.

For this purpose a tissue cutting device according to claim 1 is provided, wherein the device is of an at least partly spherical shape and structured and arranged to be inserted in a temporary delivery shape through the vascular system into a body vessel adjacent to the heart and/or into the heart and to be subsequently subjected to a change of shape, from said temporary delivery shape via an expanded delivered shape to a further expanded shape, extending at least beyond an inner surface of said tissue, in order to create cutting action configured for cutting said heart tissue and/or said body vessel.

Advantageous features of the invention are defined in the dependent claims.

BRIEF DESCRIPTION OF THE DRAWINGS

The invention will now be described in further detail by way of example under reference to the accompanying drawings, on which:

FIGS. 4*a*-4*c* are perspective schematic views of a tissue cutting device according to an embodiment of the invention, wherein FIG. 4*a* shows the tissue cutting device in a first, temporary shape, FIG. 4*b* shows the tissue cutting device in a second, permanent shape, and FIG. 4*c* illustrates the tissue cutting device having sharp edges;

FIGS. 5*a*-5*b* show the tissue cutting device of FIGS. 4*a*-4*b* inserted in a body vessel;

FIGS. 6-14*f* show different embodiments of the tissue cutting device;

FIG. 17*b* shows the tissue cutting device of FIG. 15 after the device has penetrated the heart wall and has completed a change of shape similarly to FIG. 17*a*, but where the cutting arm of the device abuts another tissue cutting device inserted into another vessel;

FIG. 17*c* is a schematic view showing the tissue cutting device of FIG. 15 after it has completed its change of shape, wherein the tissue lesion creating device has been inserted into the left superior pulmonary-vein and the cutting arm is extended to the left atrial appendage opening;

FIG. 17*d* is a perspective view with a section of the vessel and the heart wall cut-off and shows the tissue cutting device of FIG. 15 after the device has penetrated the heart wall and has completed a change of shape similarly to FIG. 17*a*, but where the tissue cutting device comprises an atrial end instead of the cutting arm;

FIGS. 18-25 are schematic views of the heart showing tissue cutting devices inserted into different blood vessels adjacent the heart and illustrating cutting patterns achieved by these tissue lesion creating devices, wherein FIGS. 18-19 and 24-25 show a cross-section that has been cut through the atria of the heart and FIGS. 20-23 show the atria of the heart from the outside of the heart seen from behind;

FIGS. 26a-26b shows a cross-section of the left atrial appendage and a tissue cutting device inserted into the left atrial appendage, wherein FIG. 26a shows the tissue cutting device before a change of shape has started and FIG. 26b shows the tissue cutting device after the change of shape;

FIGS. 27-28 illustrate tissue cutting devices inserted into the left atrial appendage and the right atrial appendage, the figures showing a cross-section that has been cut through the atria of the heart;

DETAILED DESCRIPTION OF THE INVENTION

Figure 1:
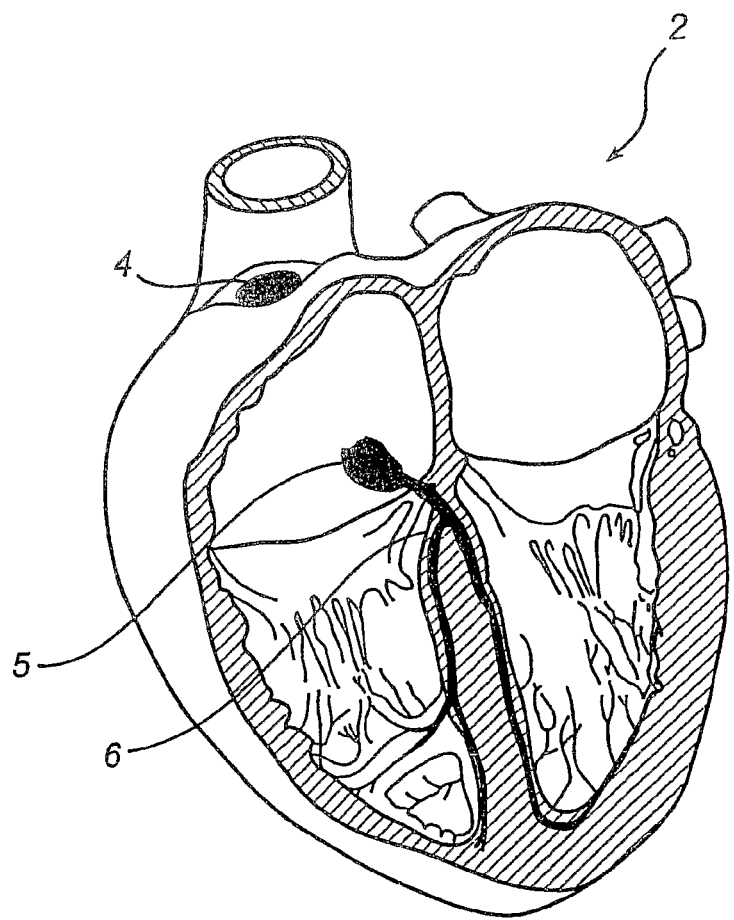
FIG. 1 is a schematic view of the transmission of electrical signals in the heart.
Figure 2:
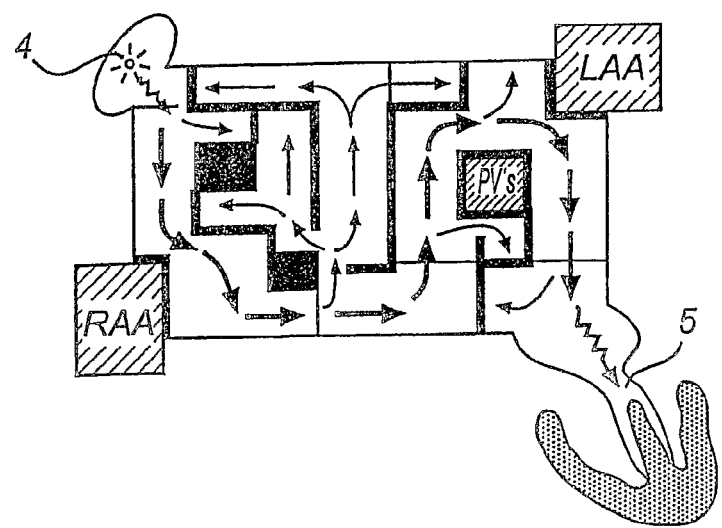
FIG. 2 is a schematic view of a pattern of cutting tissue of the heart wall according to the Maze-procedure for treating disorders to the heart rhythm regulation system.
Figure 3:
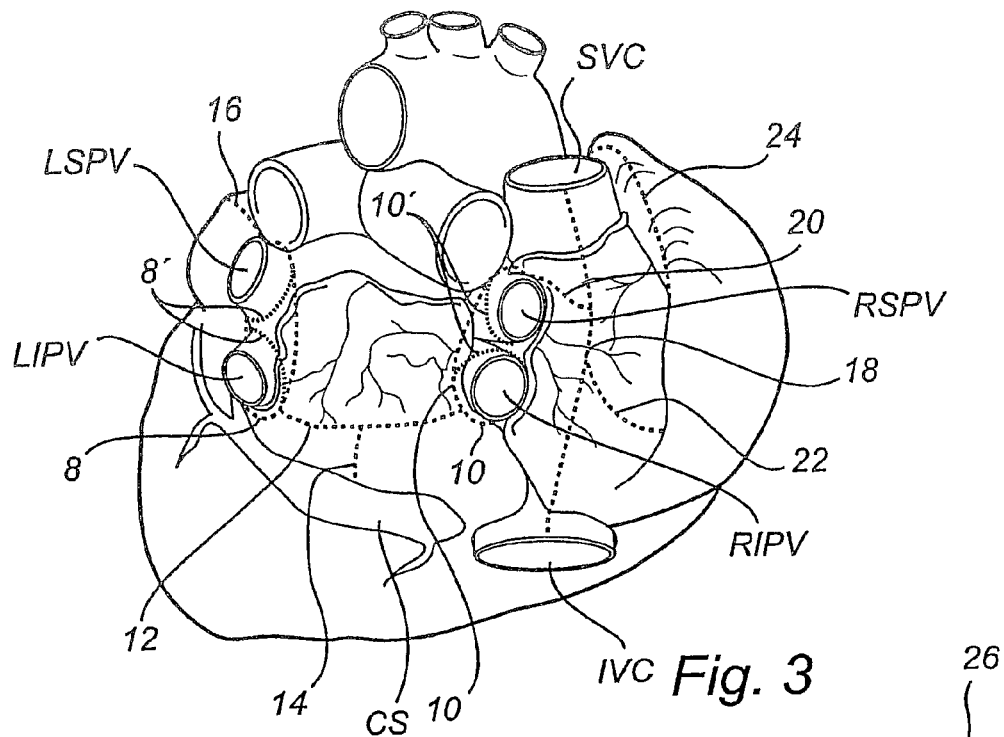
FIG. 3 is a schematic view of a simplified pattern according to the Maze III-procedure, wherein the heart is seen from behind.

Referring now to FIGS. 1-3, the problems of disorders to the heart rhythm regulation system and the leading current method of treating these problems will be described. In FIG. 1, a heart 2 is shown and the controlling of the heart rhythm is indicated. The heart rhythm is normally controlled from the sinoatrial node 4. The sinoatrial node 4 transmits electrical signals which are propagated through the heart wall by means of special cells forming an electrical pathway. The electrical signals following the electrical pathway will coordinate the heart muscle cells for almost simultaneous and coordinated contraction of the cells in a heart atrium and heart ventricle. The normal conduction of electrical impulses through the heart starts in the sinoatrial node 4, travels across the right atrium, the atrioventricular node 5, the bundles of His 6 and thereafter spread across the ventricular muscle mass. In a disordered situation, electrical signals are started in heart cells outside the sinoatrial node 4, in so called ectopic sites. These electrical signals will disturb the coordination of the heart muscle cells. If several ectopic sites are present, the signal transmission becomes chaotic. This will be the cause of arrhythmic diseases, such as atrial fibrillation and atrial flutter.

An existing method for treating these diseases is based on isolating the ectopic sites in order to prevent the electrical signals started in these ectopic sites to propagate in the heart wall. Thus, the heart wall is cut completely through for interrupting the coupling between cells that transmit erratic electrical signals. The thus created lesion will be healed with fibrous tissue, which is unable to transmit electrical signals. Thus, the path of the electrical signals is blocked by this lesion. However, since the location of the ectopic sites may not always be known and may be difficult to determine or since there might be multiple ectopic sites, a special cutting pattern has been developed, which will effectively isolate ectopic sites. Thus, the same pattern may always be used regardless of the specific locations of the ectopic sites in each individual case. The procedure is called the "Maze"-procedure in view of the complicated cutting pattern. In FIG. 2, the Maze-pattern is illustrated.

However, as is evident from FIG. 2, the cutting pattern is extensive and complex and requires a difficult surgery. Thus, the Maze-pattern has been evolved in order to minimize the required cuttings and simplify the pattern as much as possible. Currently, a Maze III-pattern is used, as shown in FIG. 3. This pattern is not as complicated, but would still effectively isolate the ectopic sites in most cases. The Maze III-pattern comprises a cut 8 around the left superior pulmonary vein (LSPV) and the left inferior pulmonary vein (LIPV) and a corresponding cut 10 around the right superior pulmonary vein (RSPV) and the right inferior pulmonary vein (RSPV); a cut 12 connecting the two cuts 8 and 10 around the pulmonary veins (PV); a cut 14 from this connecting cut to the coronary sinus (CS); a cut 16 from the left PVs to the left atrial appendage; a cut 18 from the inferior vena cava (IVC) to the superior vena cava (SVC); a cut 20 connecting the cut 10 around the right PVs and the cut 18 between the IVC and the SVC; a cut 22 from the cut 18 between the IVC and the SVC along the right lateral atrium wall; and a cut 24 isolating the right atrial appendage. Thus, a pattern, which is less complex and which effectively isolates the ectopic sites, has been established. In some cases, all cuts may not be needed. For example, the occurrence of ectopic sites often starts around the orifices of the PVs and, therefore, it may be sufficient to make the cuts 8, 10 around the PVs. Further, as indicated with the lines 8' and 10', the cuts around the PVs may be done along each PV orifice instead of in pairs.

According to the invention, there is provided a possibility of cutting through the heart wall in a new manner. Thus, a similar pattern to the Maze III-pattern should also be achieved according to this new manner. However, as mentioned above, it may not in all cases be required that all cuts of the Maze III-pattern are made.

Figure 4A:
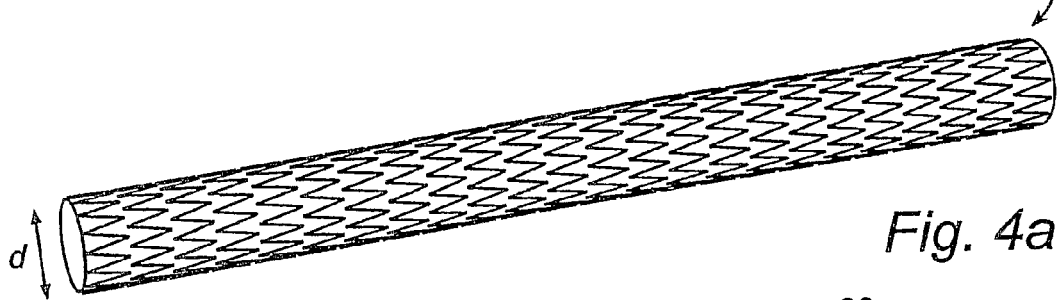
Figure 4B:
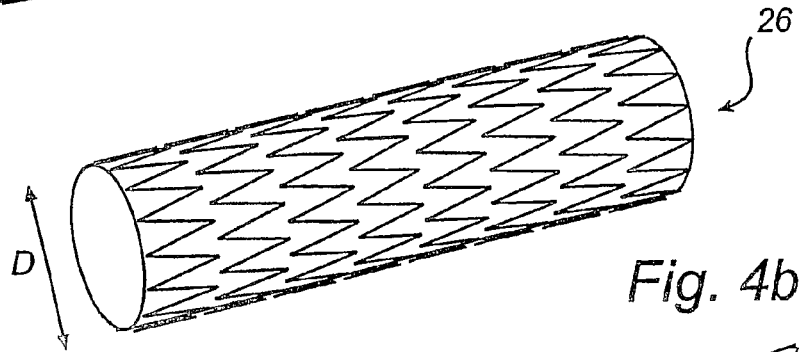

Referring now to FIGS. 4-5, a heart wall tissue lesion creating cutting device 26 according to an embodiment of the invention will be described and the new manner of performing the cuts through the heart wall will be explained. The heart wall tissue lesion creating cutting device 26 (hereinafter called cutting device) is shown in FIG. 4a in a first state, in which the cutting device 26 is tubular and has a first diameter d. The cutting device 26 is shown in FIG. 4b in a second state, in which the cutting device 26 is tubular and has a second diameter D, which is larger than the first diameter d. The cutting device 26 is formed of a shape memory material, which has the ability of memorizing a permanent shape that may significantly differ from a temporary shape. The shape memory material will transfer from its temporary to its memorized, permanent shape as a response to a suitable stimulus. The stimulus may be exposure to a raised temperature, such as a temperature above e.g. 30° C. that may be caused by the body temperature. The stimulus may suitably be combined with the release of a restraining means, which may keep the shape memory material from assuming its permanent shape.

The shape memory material allows designing a cutting device 26 that may be contracted into a small, temporary shape before insertion into a patient. Thus, the cutting device 26 may be inserted in this temporary shape to the heart of a patient through the vascular system. The temporary shape of the cutting device 26 is also flexible, whereby guiding the cutting device 26 through the vascular system is facilitated. This insertion of the cutting device 26 may be performed with well-known percutaneous catheter techniques. This is an unaggressive procedure and may be performed on a beating heart. Thus, the cutting device 26 may readily be positioned at a desired position within the vascular system adjacent heart wall tissue to be treated. The cutting device 26 may then be allowed to transfer to its memorized, permanent shape when inserted to the desired position in a blood vessel.

As shown in FIG. 5a, the cutting device 26 is inserted in its temporary shape in a desired position within a blood vessel 28. As a response to a stimulus, e.g. the body temperature, the cutting device 26 will then strive towards changing its shape and obtaining the permanent shape. The memorized, permanent shape of the cutting device 26 will not fit into the blood vessel 28, whereby the cutting device 26 will force itself through surrounding tissue for obtaining the permanent shape, as shown in FIG. 5b. In this way, the cutting device 26 will first penetrate the vessel wall and thereafter tissue surrounding the blood vessel 28. Tissue cells that are penetrated will be killed, which will start a healing reaction in the body. Where the cutting device 26 is placed in a desired position to change shape through heart wall tissue, cells that are able to transmit electrical signals may thus be killed. The healing process will not restore the ability to transmit electrical signals and, therefore, the cutting device 26 will reduce the ability of transmitting electrical signals through the heart wall. By placing several cutting devices intelligently and designing the permanent shape of the cutting devices 26 accordingly, the cutting devices 26 may penetrate heart wall tissue to create a pattern of cuts corresponding to the Maze III-pattern. An example of a shape memory material, is Nitinol, which is an alloy composed of nickel (54-60%) and titanium. Small traces of chrome, cobalt, magnesium and iron may also be present. This alloy uses a martensitic phase transition for recovering the permanent shape. Shape memory materials may also be formed of shape memory polymers, wherein the shape-memory effect is based on a glass transition or a melting point. Such shape memory polymers may be produced by forming polymers of materials or combinations of materials having suitable properties. For example, a shape memory polymer may be created of oligo(e-caprolactone) dimethacrylate combined with n-butyl acrylate. Also, biodegradable or bioresorbable materials may be used for forming these shape memory polymers. In this way, the cutting device 26 may be designed such that it will be degraded or absorbed by the body after it has performed its change of shape. For example, a polylactic acid polymer and/or a polyglycolic acid polymer, poly (e-caprolactone) or polydioxanone may be used for forming a shape memory polymer that is biodegradable. A special feature of the resorbable shape memory polymers is that these will disappear from the tissue after having had its function, limiting potential negative effects of otherwise remaining polymer or Nitinol materials, such as perforations and damage to other adjacent tissues, like lungs, oesophagus and great vessels like the aorta.

The cutting device 26 may alternatively be formed to exhibit an elasticity such that it has a strive towards its permanent shape. This may be accomplished by forming the cutting device 26 to a spiral-shape in e.g. stainless steel or a magnesium alloy which is biodegradable.

The cutting device 26 may be tubular in both its temporary shape and its permanent shape, as shown in FIGS. 4-5. However, the shape memory may be used for bringing the cutting device 26 between any shapes. Some examples of shapes that are at least not entirely tubular will be given below. The shape of the cutting device 26 in its first state is preferably compact to facilitate insertion of the cutting device 26 through the vascular system. Thus, a tubular shape is suitable, but other shapes may be just as suitable. Further, the shape of the cutting device 26 in its second state is designed such that the change of shape will provide penetration of specific heart tissue in order to block propagation of undesired electrical signals. Also, the shape of the cutting device 26 in its second state may be adjusted for fixing the cutting device 26 to its desired position within the body.

The cutting device 26 may be constructed of a net; i.e. its shape may comprise meshes or loops. This implies that a solid surface need not penetrate tissue, whereby the penetration through tissue and the forming of different shapes of the cutting device 26 will be facilitated.

Figure 4C:
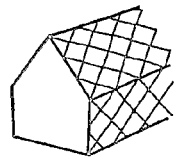

The edges of the cutting device 26 facing the tissue to be penetrated may be made especially sharp to increase its effectiveness, as illustrated in FIG. 4c. Another feature is to cover the surface towards the tissue to be penetrated with drugs that increase the cutting effect or prohibit the thickening of the wall of the vessel in which the device is inserted. Examples of such drugs are ciclosporin, taxiferol, rapamycin, tacrolimus, alcohol, glutaraldehyde, formaldehyde, and proteolytic enzymes like collagenase. Collagenase is effective in breaking down tissue and especially fibrin tissue, which is otherwise difficult to penetrate. Therefore, covering the surface of the cutting device 26 with collagenase would particularly speed up the process of penetrating tissue. The drugs are attached to the surface of the cutting device 26 according to well-known methods of attaching drugs to medical devices. One such method is embedding drugs into or under layers of polymers, which cover the surface. Of course, other methods may be used. Similarly, drugs preventing thrombosis and increasing in-growth of endothelium on the endothelial surface after penetration of the cutting device 26 may be attached to the cutting device 26. Such drugs would be e.g. Endothelium Growth Factor, and Heparin. Also, other drugs designed to treat arrhythmias may be attached to the cutting device surface. Such drugs are e.g. amiodarone and sotalol.

Preferably, the inside of the cutting device 26 inserted into a blood vessel will be in contact with the blood stream inside the blood vessel. Such inside surface of the cutting device 26 may as well be covered with antithrombotic drugs. Such drugs would be e.g. Heparin, Klopidogrel, Enoxaparin, Ticlopidin, Abciximab, and Tirofiban.

Another way to increase the effectiveness of the cutting device 26 is to attach a metallic part of the cutting device 26 to electrical currency, which would provide a heating of the cutting device 26. Thereby, tissue may also be killed by this heating, enhancing the effect of the cutting device 26. Further, the force driving the change of shape will also be increased, speeding up the shape change of the cutting device.

Referring now to FIGS. 6-12, cutting devices that are specifically suited for insertion into specific blood vessels will be described. All or some of these cutting devices may be delivered in a kit to be used for treatment of a disorder of the heart rhythm regulation system. Alternatively, the cutting devices may be delivered separately. Then, the required cutting devices for an operation may be assembled for each specific patient or for a specific disease pattern. The cutting devices may also be provided in different sizes to suit the size of the heart and the vessels of the patient. Thus, a complete kit is assembled from devices designed to fit to the anatomical conditions of the actual treatment locations in order to achieve optimal results.

Referring now to FIG. 6, a first cutting device 30 adapted to be inserted into the CS is shown. This first cutting device 30 has a tubular part 32, which is pre-bent to assume a curved shape to fit to the curvature of the CS. Thus, the first cutting device 30 will assume a curved temporary shape within the CS. Further, the cross-section of the first cutting device 30 is smaller in a distal end 34 to be inserted furthest into the CS than at a proximal end 36 to be placed at the orifice of the CS. The cross-section of the first cutting device 30 may be elliptic or circular or may vary along the length of the cutting device 30. The first cutting device 30 may be designed to change shape such that the cross-section of the first cutting device 30 is mainly expanded at the inside of the curve towards the heart wall. Thus, the first cutting device 30 will penetrate the heart wall tissue adjacent the CS. Moreover, the first cutting device 30 has a length of at least the distance between the two inferior PVs. It can also be designed to cover the distance from the orifice of the CS and past the LIPV. The first cutting device 30 may serve as support for other cutting devices inserted into other blood vessels adjacent the heart, as explained in more detail later on. In this case, it may suffice that the first cutting device 30 is fixated into the CS wall. There may also not be any need for the first cutting device 30 penetrating heart tissue itself, when treating the PV orifices solely. The first cutting device 30 may also comprise one or more cutting arms (not shown), which, in the temporary shape of the first cutting device 30, extend along the tubular part 32 or in an axial direction of the tubular part 32. Further, the first cutting device 30 may be arranged to change shape such that the one or more cutting arms extend in a radial direction from the tubular part 32. Thus, during the change of shape, the one or more cutting arms will penetrate through heart tissue adjacent the CS.

Referring now to FIGS. 1a-b, a second cutting device 38 adapted to be inserted into the LIPV is shown. In FIG. 7a, the second cutting device 38 is illustrated in a contracted, temporary shape, and in FIG. 7b, the second cutting device 38 is illustrated in an expanded state. This second cutting device 38 is adapted to be inserted at the orifice of the LIPV into the heart. The second cutting device 38 has a tubular part 40. As shown in FIGS. 7a-b, the tubular part 40 may comprise two or more portions. A first portion 42 of the tubular part 40 to be inserted closest to the LIPV orifice is arranged to change shape to circumferentially penetrate the LIPV wall and penetrate heart wall tissue around the LIPV. Thus, an effective block against propagation of undesired electrical signals is created around the orifice of the LIPV. A second portion 44 of the tubular part 40 is arranged to change shape to abut the vessel wall or only penetrate into the vessel wall. Thus, this second portion 44 will only serve to stabilize the second cutting device 38 in the axial direction and it may not be needed. The first 42 and second portions 44 of the tubular part 40 are interconnected by a connecting member 46, in the form of bars or wires. The first portion 42 may be funnel-shaped having a larger diameter at the end closest to the orifice of the LIPV. The funnel-shape wall partly compensate for the increasing diameter of the LIPV towards the orifice. However, the diameter of the funnel-shaped first portion 42 may increase to a larger extent than the LIPV towards the orifice, whereby the second cutting device 38 will penetrate deeper into the heart tissue at the orifice end. Further, the smaller end of the funnel-shaped first portion 42 may be arranged to merely penetrate into or abut the vessel wall for stabilizing the second cutting device 38 in its axial direction. The first portion 42 of the tubular part 40 may extend from the orifice of the LIPV inside the heart to a position outside the heart wall, whereby the smaller end of the funnel-shaped first portion is arranged outside the heart wall. Thus, the first portion 42 may still penetrate through heart tissue throughout the entire thickness of the heart wall, even though the smaller end of the funnel-shaped first portion merely penetrates into or abuts the vessel wall.

The tubular part 40 is typically arranged to change shape to penetrate a circular area of tissue around and adjacent the LIPV. However, the tubular part 40 may also be arranged to change shape to expand to such a degree that it would come in contact with the first cutting device 30 inserted into the CS, whereby the heart tissue between the LIPV and the CS will be effectively treated. Then, the first 30 and the second cutting devices 38 in contact with each other will stabilize each other's positions.

The end of the tubular part 40 forms an atrial end 48, which is arranged to be inserted extending into the heart atrium when the second cutting device 38 is inserted into its desired position. Thus, as shown in FIG. 7a, during insertion of the second cutting device 38, the atrial end 48 will extend in an axial direction of the tubular part 40. However, when the second cutting device 38 changes shape the atrial end 48 will be folded outwardly extending in a radial direction to the tubular part 40, as shown in FIG. 7b. The atrial end 48 will during its change of shape penetrate into the heart wall for fixing the position of the second cutting device 38 and for forming a block against undesired electrical signals around the orifice of the LIPV. This atrial end 48 may be formed of, for instance, a multiple of arches overlapping each other. Each such arch will penetrate through a piece of tissue adjacent the LIPV orifice and leave a small islet of separated tissue, after having penetrated through the tissue.

The second cutting device 38 may also comprise a cutting arm 50. The cutting arm 50 is attached to the end of the tubular part 40 to be inserted closest to the LIPV orifice. In the temporary shape of the second cutting device 38, as shown in FIG. 7a, the cutting arm 50 extends in an axial direction of the tubular part 40 for facilitating insertion of the second cutting device 38. In the permanent shape of the second cutting device 38, the cutting arm 50 extends in a radial direction of the tubular part 40, as shown in FIG. 7b. When the second cutting device 38 is placed in its desired position, the cutting arm 50 will extend into the heart atrium. Thus, during the change of shape of the second cutting device 38, the cutting arm 50 will penetrate through the heart wall tissue to assume a position extending radially from the tubular part 40. This effect of the cutting arm 50 will be explained in more detail below with reference to FIGS. 14-16. The cutting arm 50 will create a line blocking propagation of undesired electrical signals in the heart wall. Thus, the cutting arm 50 could make cutting lines for forming the desired cutting pattern. The cutting arm 50 of the second cutting device 38 may be arranged to make a cut from the LIPV to the CS. Thus, the cutting arm 50 could come in contact with the first cutting device 30 inserted into the CS, which would fixate the position of the cutting arm 50. This cutting arm 50 could also comprise a trough 52 in the portion of the cutting arm 50 that will contact the first cutting device 38. This ensures that the cutting arm 50 beyond the trough 52 may extend through the heart wall from the CS to the mitral valve. The second cutting device 38 may also have further cutting arms (not shown) to be extended towards any of the other PVs.

The cutting arm is constructed of sequential loops in a longitudinal direction of the arm. As these loops penetrate through the heart wall tissue, closed loops of lesion lines will be formed, creating islets of untreated tissue inside them. The lesion lines will present a block of propagation of electrical signals.

Figure 8:
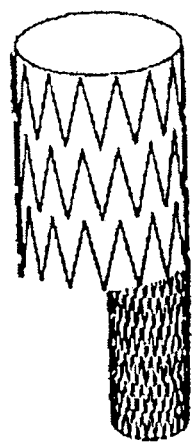
Figure 8:
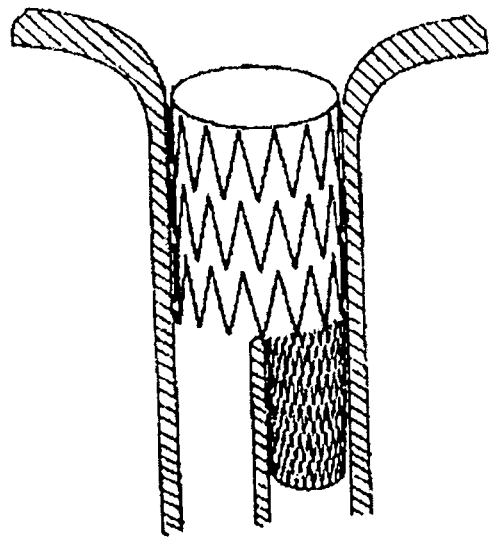
Figure 8:
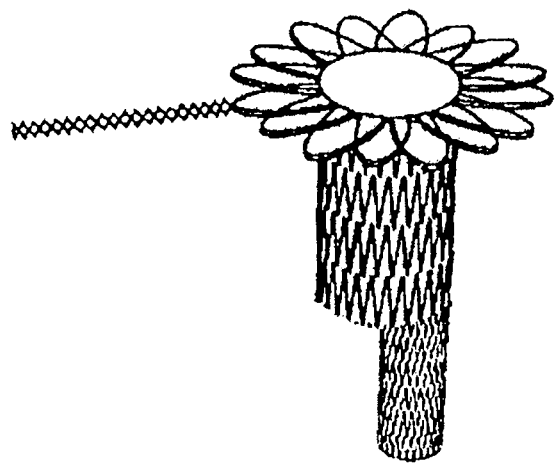

In another embodiment of the present invention, according to FIG. 8, the tubular part may also comprise two segments connected to each other axially where the first part, closest to the left atrium, is considerably larger in diameter than the second, deeper part that is supposed to fit into a smaller branch of the pulmonary vein system. Thus this embodiment would look like a pair of trousers with one leg cut of in the groin area. In this embodiment the smaller segment in the deeper smaller vein would give excellent support for the larger part closest to the ostium of the pulmonary vein, prohibiting this part to migrate into the left atrium, according to FIG. 8b. This embodiment may naturally also comprise the atrial end 48 and the cutting arm 50, according to FIG. 8c. The tubular part may comprise at least two axially separated tubular portions, which are interconnected by a connecting member. These tubular portions may then be structured and arranged to change shape to expand to different diameters or be transversely expandable to different degrees. This may be used for the same purpose as the funnel-shape described above. Thus, at least one of the tubular portions may be structured and arranged to change shape to expand its diameter to correspond to the diameter of the vessel where it is placed. In this way, this tubular portion will only serve to keep the device in place. Another tubular portion may then change shape to penetrate the heart tissue for the treatment purposes, further, the connecting member may be one or more bars or wires connecting the tubular portions.

Figures 9, 10:
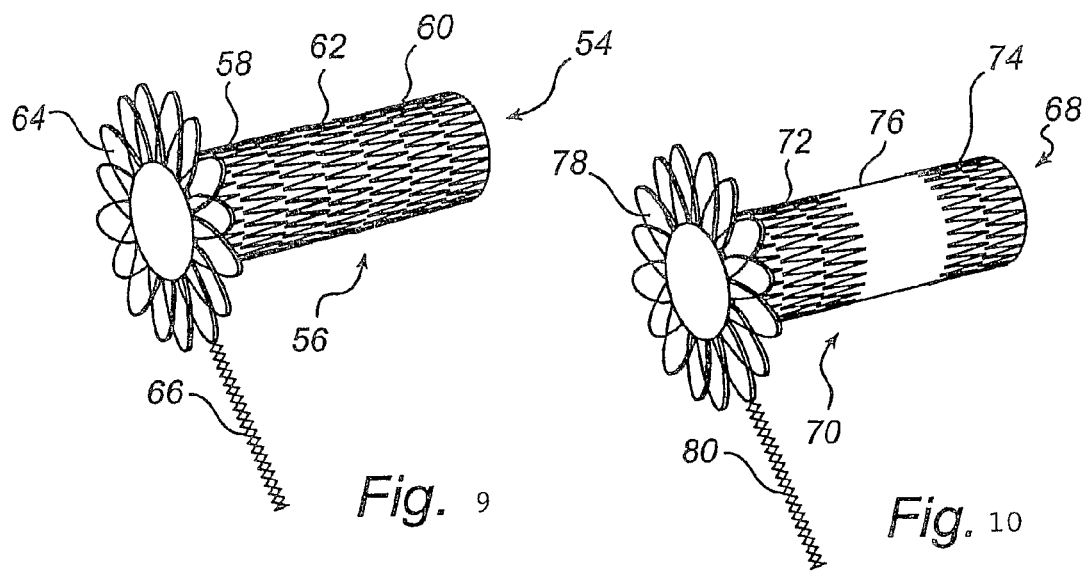

Referring now to FIG. 9, a third cutting device 54 adapted to be inserted into the RIPV is shown. This third cutting device 54 presents similar features as the second cutting device 38. Thus, the third cutting device 54 also comprises a tubular part 56, which also may consist of two or more tubular portions 58, 60, which are interconnected by a connecting member 62. The tubular part 56 of the third cutting device 54 presents similar features as the tubular part 40 of the second cutting device 38. The third cutting device 54 also comprises an atrial end 64, similar to the atrial end 48 of the second cutting device 38. Moreover, the third cutting device 54 also comprises a cutting arm 66, similar to the cutting arm 50 of the second cutting device 38. This cutting arm 66 is arranged to change shape in order to extend radially from the tubular part 56 towards the CS and come in contact with the first cutting device 30 inserted into the CS close to the orifice of the CS. The cutting arm 66 of the third cutting device 54 is normally shorter than the cutting arm 50 of the second cutting device 38 permitting adaptation to the different distance between the third cutting device 54 and the CS. Further, the cutting arm 66 of the third cutting device 54 need not have a trough, since, in this case, there is no need of treating heart tissue beyond the CS. The third cutting device 54 may also comprise other cutting arms (not shown) extending towards any of the other PVs.

Referring now to FIG. 10, a fourth cutting device 68 adapted to be inserted into the LSPV is shown. This fourth cutting device 68 presents similar features as the second and third cutting devices 38, 54. Thus, the fourth cutting device 68 also comprises a tubular part 70, which may consist of two or more tubular portions 72, 74, which are interconnected by a connecting member 76. The tubular part 70 of the fourth cutting device 68 presents similar features as the tubular part 40, 56 of the second and third cutting devices 38, 54. The fourth cutting device 68 also comprises an atrial end 78, similar to the atrial end 48, 64 of the second and third cutting devices 38, 54. Moreover, the fourth cutting device 68 also comprises a cutting arm 80, similar to the cutting arm 66 of the third cutting device 54. This cutting arm 80 is arranged to change shape in order to extend radially from the tubular part 70 towards the LIPV and come in contact with the second cutting device 38 inserted into the LIPV. The cutting arm 80 of the fourth cutting device 68 is normally very short permitting adaptation to the short distance between the LSPV and the LIPV, which is typically a few millimeters to a centimeter. The fourth cutting device 68 may also comprise another cutting arm (not shown), which after the change of shape of the fourth cutting device 68 would extend towards the left atrium appendage orifice.

Figures 11, 12:
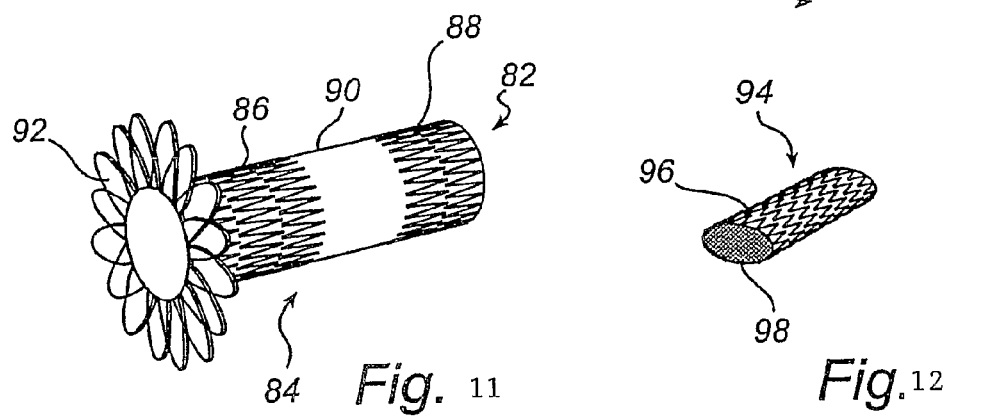

Referring now to FIG. 11, a fifth cutting device 82 adapted to be inserted into the RSPV is shown. This fifth cutting device 82 presents similar features as the second, third and fourth cutting devices 38, 54, 68. Thus, the fifth cutting device 82 also comprises a tubular part 84, which may consist of two or more tubular portions 86, 88, which are interconnected by a connecting member 90. The tubular part 84 of the fifth cutting device 82 presents similar features as the tubular part 40, 56, 70 of the second, third and fourth cutting devices 38, 54, 68. The fifth cutting device 82 also comprises an atrial end 92, similar to the atrial end 48, 64, 78 of the second, third and fourth cutting devices 38, 54, 68. However, the fifth cutting device 82 would normally not comprise any cutting arm, since it would normally be sufficient to penetrate the tissue around the RSPV. The fifth cutting device 82 may anyhow comprise a cutting arm adapted to extend towards any of the other PVs.

Referring now to FIG. 12, a sixth cutting device 94 adapted to be inserted into the left atrial appendage (LAA) or the right atrial appendage (RAA) is shown. The sixth cutting device 94 comprises a tubular part 96, which has an elliptic cross-section to fit into the elliptic form of the orifice of the LAA. A sixth cutting device 94 adapted to be inserted into the RAA will have a tubular part 96 with a less elliptic cross-section to fit the orifice of the RAA. The sixth cutting device 94 is adapted to be inserted into the orifice of the LAA inside the left atrium or into the orifice of the RAA inside the right atrium. The sixth cutting device 94 will further change shape by expanding its tubular part 96 through the atrial wall at the orifice. Thus, the LAA or the RAA will be completely cut off from electrical contact with the rest of the heart tissue. The tubular part 96 of the sixth cutting device 94 may be quite short extending from the orifice of the atrial appendage along its wall into the atrial appendage. Further, the tubular part 96 may be funnel-shaped, whereby a portion of the tubular part 96 may be designed to change shape in order to assume a cross-section that will not penetrate through the entire heart wall. This portion of the tubular part 96 may then serve to keep the sixth cutting device 94 in place. Further, another portion of the tubular part 96 will penetrate through the entire heart wall in order to effectively electrically isolate the atrial appendage from the rest of the heart. A sixth cutting device 94 adapted to be inserted into the LAA may comprise a cutting arm (not shown), which is adapted to change shape to penetrate through the heart tissue extending from the LAA to a fourth cutting device 68 inserted into the LSPV. Further, a sixth cutting device 94 adapted to be inserted into the LAA may comprise a film 98 covering an end of the tubular part 96 to be inserted closest to the orifice of the LAA. When the tubular part 96 is expanded into the heart wall, the film 98 will cover the orifice of the LAA, excluding the LAA from the blood circulating through the heart, whereby a dislocation of thrombus and dot formation in the LAA will be avoided.

Figures 13A, 13B:
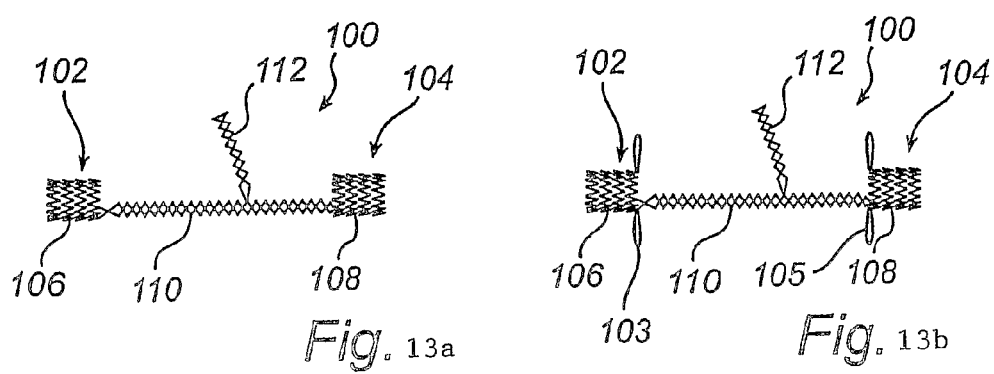

Referring now to FIG. 13a, a seventh cutting device 100 adapted to be inserted into the IVC and the SVC is shown. The seventh cutting device 100 comprises two pieces 102, 104, a first piece 102 to be inserted into the SVC and a second piece 104 to be inserted into the IVC. Each piece 102, 104 of the seventh cutting device 100 comprises a tubular part 106, 108, which presents similar features as the tubular part 40, 56, 70, 84 of the second, third, fourth, and fifth cutting devices 38, 54, 68, 82. Each tubular part 106, 108 may advantageously be funnel-shaped, wherein an end having the largest cross-section is adapted to be inserted closest to the orifice of the IVC or the SVC, respectively. The seventh cutting device 100 further comprises a connecting cutting arm 110. The seventh cutting device 100 is arranged to change shape such that this connecting cutting arm 110 will extend between the tubular part 106 of the first piece 102 inserted into the SVC and the tubular part 108 of the second piece 104 inserted into the IVC. This change of shape will cause the connecting cutting arm 110 to penetrate through the lateral right atrium heart wall tissue between the orifice of the SVC and the orifice of the IVC. The connecting cutting arm 110 may be attached to any one of the first and the second piece 102, 104 of the seventh cutting device 100, and preferably the connecting cutting arm 110 is attached to both the first and the second pieces 102, 104. If the connecting cutting arm 110 is only attached to one of the first and second pieces 102, 104, it will connect the first and the second pieces 102, 104 together after the change of shape has occurred. The connecting cutting arm 110 may comprise a branch 112, which, after the change of shape of the seventh cutting device 100, will extend from a point of the connecting cutting arm 110 laterally through the right atrial wall, whereby this branch 112 will penetrate the right lateral wall of the right atrium. As for the cutting arms, the branch 112 may be constructed of one loop or several sequential loops in a longitudinal direction of the branch 112. The seventh cutting device 100 may comprise a further cutting arm (not shown), which may be attached to the tubular part 108 of the second piece 104 that is inserted into the IVC. The seventh cutting device 100 is then arranged to change shape such that this further cutting arm will extend from the tubular part 108 of the second piece 104 inserted into the IVC towards and into the orifice of the CS. This change of shape will cause the further cutting arm to penetrate through the heart wall tissue between the orifice of the IVC and CS. This further cutting arm may alternatively be arranged as a further branch of the connecting cutting arm 110. The seventh cutting device 100 may, in a simple version for treating mild forms of disorders to the heart rhythm regulation system, consist of only the first piece 102 adapted to be inserted into the SVC, which first piece 102 may or may not comprise a cutting arm. As shown in FIG. 13b, the first and second pieces 102, 104 may also each comprise an atrial end 103, 105, similar to the atrial end 48, 64, 78, 92 of the second, third, fourth, and fifth cutting devices 38, 54, 68, 82.

In still another embodiment the heart tissue cutting device is located inside the atrium to be treated. The device then would be made out of at least one thread or wire, according to FIGS. 14a to f. If the atrial device is made out of more than one wire the wires would be interconnected or braided to each other. In one of the embodiments the implanted shape of the device will assume a net-like pattern. Further the net-like pattern may form a shape that is arranged to encompass at least a portion of the atrium it is intended to treat before cutting through the wall. The net-like pattern may form a spherical form encompassing a substantial part of the atrium, according to FIG. 14a. The net-like pattern may form an ellipsoidal segment, according to FIGS. 14b to d, encompassing a substantial part of the atrium. Again the net-like pattern may form a cup-shape. Thus the device is adapted to be positioned in the upper or lower part of the atrium. The atrial device would be formed identical to at least a part of the inner surface of the atrium, only considerably larger, allowing the device to grow through the entire wall of the heart, to come outside of the atrium and thereby cutting the atrium in pieces. The cut made will be replaced continuously by scar tissue that does not conduct electrical signals. Thus, islets of atrial wall tissue containing tissue that conduct electrical signals are isolated unable to transmit erratic current to the next islet.

In the embodiment according to FIG. 14a the cutting device according to the present invention may be in form of a globulus. This globulus is placed inside the heart, such as in the left or right atrium, in a temporary shape. The cutting device is then stimulated, by for example temperature, according to above, to expand towards its memorized, permanent shape. This expansion results in that the heart tissue is cut by the cutting device according to the present invention. Tissue cells that are penetrated by the cutting device will be killed, which will start a healing reaction in the body. Where the cutting device is placed in a desired position to change shape through heart wall tissue, cells that are able to transmit electrical signals may thus be killed. The healing process will not restore the ability to transmit electrical signals and, therefore, the cutting device will reduce the ability of transmitting electrical signals through the heart wall.

Figure 14:
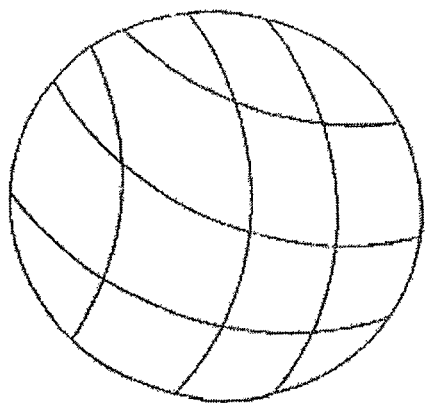
Figure 14:
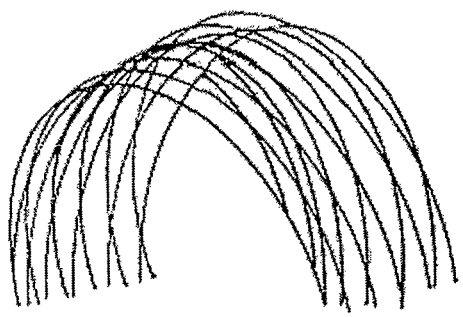
Figure 14:
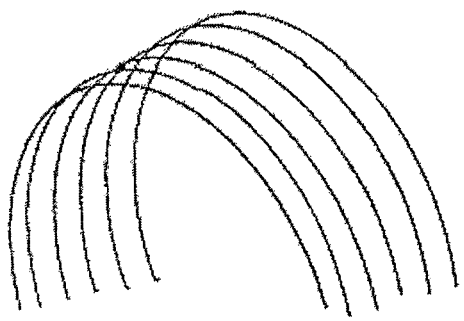
Figure 14:
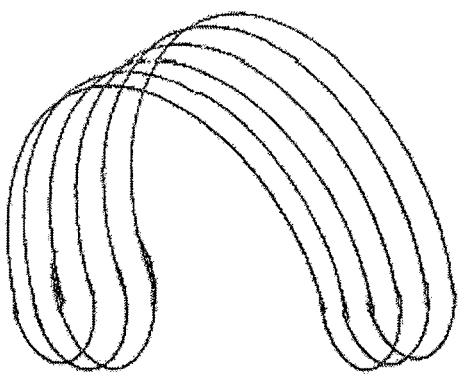
Figure 14:
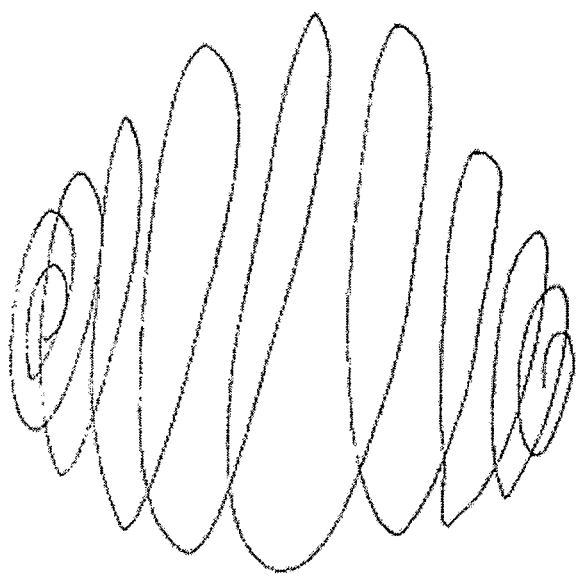
Figure 14:
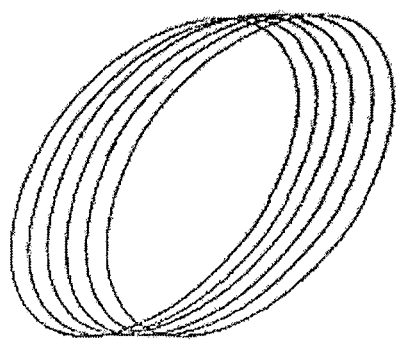

The cutting devices according to FIG. 14 may also be combined with the tubular parts of all other embodiments of the present invention, i.e. the cutting devices according to FIG. 14 may be connected with different kinds of tubular parts. These tubular parts may then for example be delivered in a body vessel adjacent the heart while the cutting device according to any of FIG. 14 is delivered inside the heart.

Figure 15:
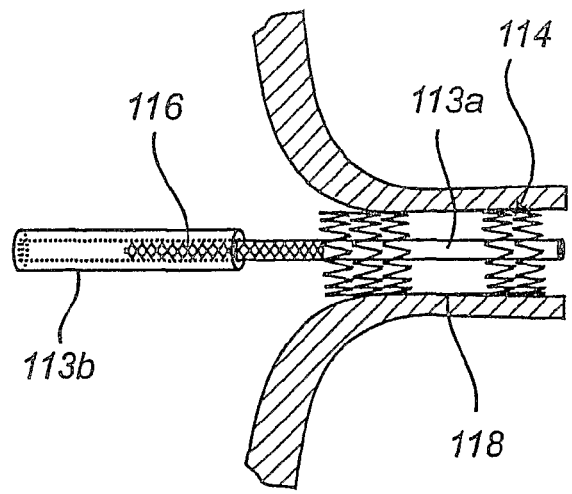
FIG. 15 shows a tissue cutting device comprising a cutting arm according to an embodiment of the invention, the tissue cutting device being shown inserted into a vessel with the cutting arm extending into a heart atrium before the tissue cutting device has started acting on the heart wall tissue.
Figure 16:
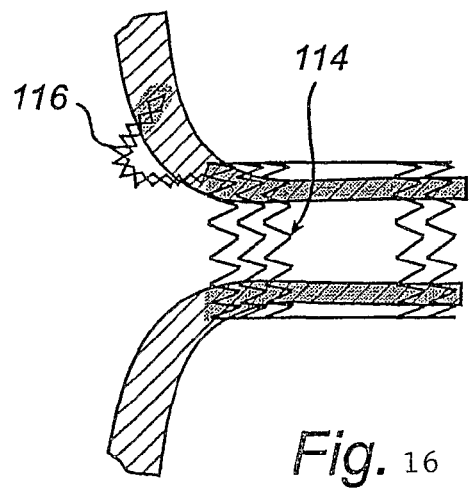
FIG. 16 shows the tissue cutting device of FIG. 15 during the time when the cutting arm penetrates a heart wall and the tissue cutting device penetrates tissue at the orifice of a vessel.
Figure 17A:
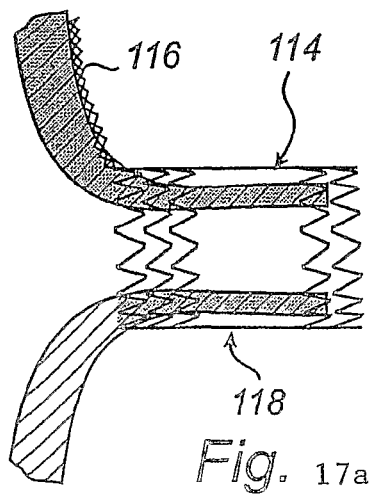
FIG. 17*a* shows the tissue cutting device of FIG. 15 after the tissue cutting device has penetrated the heart wall and the vessel wall at the orifice area and has completed a change of shape.

Referring now to FIGS. 15-17, the action of a cutting arm will be explained in further detail. In FIG. 15, a cutting device 114 comprising a cutting arm 116 has been inserted into a blood vessel at the orifice of the opening into the heart. The cutting device 114 comprises a tubular part 118, which is inserted into the blood vessel. The cutting arm 116 is attached to the tubular part 118 and extends into the heart. In FIG. 15, the cutting device 114 is shown in an intermediate shape, which it has during insertion of the cutting device 114. The cutting device 114 has carried to the illustrated position on a catheter 113a while being restrained by a restraining sheath 113b. The cutting device 114 is shown when the tubular part 118 has been released while the cutting arm 114 is still restrained by the restraining sheath 113b. Thus, a change of shape has not yet been fully commenced. In FIG. 16, the cutting device 114 is shown during its action of changing its shape. Thus, the cutting arm 116 is extending from the inside of the heart into the heart wall tissue having penetrated heart tissue during the shape-change. The cutting arm 116 will continue penetrating heart tissue in order to obtain the permanent shape of the cutting device 114. In FIG. 17a, the cutting device 114 is shown after having completed its change of shape. The tubular part 118 has now cut through the vessel wall and penetrated heart tissue around the vessel. Further, the cutting arm 116 is now completely outside the heart. Thus, the cutting arm 116 has now penetrated the entire heart wall and has therefore caused a lesion along a cutting line from the orifice of the blood vessel wall through the selected adjacent heart wall. The penetrated tissue is marked with shading in FIG. 17a, as well as in FIGS. 17b-d. In FIG. 17b, the cutting arm 116 of the cutting device 114 is shown abutting another cutting device 120, which has been inserted into another blood vessel. In this way, the cutting arm 116 has performed a lesion between the two cutting devices, whereby an effective block against propagation of undesired electrical signals has been created. The position of the cutting arm 116 is also stabilized after the change of shape by the cutting arm 116 resting on the other cutting device 120. In, FIG. 17*c*, the cutting device 114 is shown inserted into the LSPV, and the cutting arm 116 has been extended leaning into the orifice of the LAA and thereby penetrating the atrial wall between the LAA, and the LSPV. In addition to the cutting of the cutting arm 116, the tubular part 118 of the cutting device 114 inserted inside the vessel has treated the vessel wall adjacent to the orifice, which often contains ectopic sites. In FIG. 17*d*, the cutting device 114 is shown comprising an atrial end 121, which has penetrated the tissue around the orifice of the blood vessel.

Figure 18:
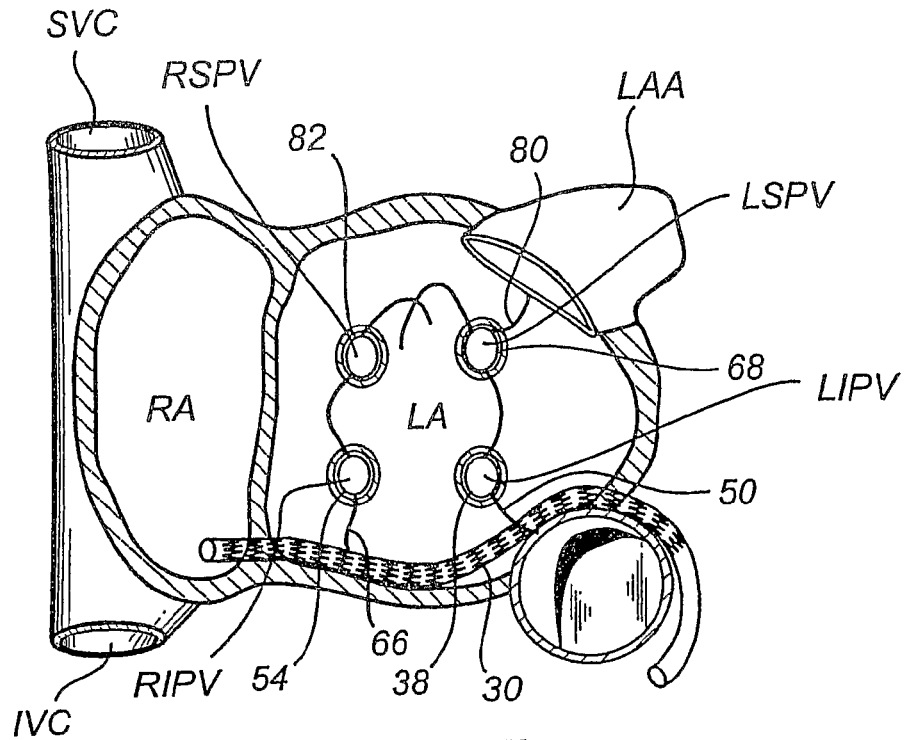

Referring now to FIGS. 18-28, there is shown cutting patterns being obtained in a few different embodiments, illustrating a few examples of sets of cutting devices being inserted into blood vessels adjacent the heart and the treatment obtained by these sets of cutting devices. The treatment needed may differ from patient to patient and other patterns may be conceivable using the concept of inserting cutting devices into blood vessels adjacent the heart. In FIG. 18, the first, second, third, fourth and fifth cutting devices 30, 38, 54, 68, 82 having been inserted into the four PVs are shown. The cutting devices 30, 38, 54, 68, 82 are shown in an intermediate shape, which they present shortly after having been delivered to the desired positions and before any penetration of heart wall tissue has begun. The tubular parts 40, 56, 70, 84 of the second, third, fourth and fifth cutting devices 38, 54, 68, 82 have expanded to abut the wall of its respective PV. The cutting arms of the second, third, fourth and fifth cutting devices 38, 54, 68*r* 82 have been diverted from the axial direction of the tubular part to abut the inside of left atrial wall of the heart. The second cutting device 38 inserted into the LIPV is shown having a cutting arm 50 extending to the mitral valve. The third cutting device 54 inserted into the RIPV has a cutting arm 66 extending to the CS. Thus, instead of forming the cuts 12 and 14 according to FIG. 3, cuts are formed from the LIPV and the RIPV to the CS. These cuts 12 and 14 are very difficult to accomplish using the technique of inserting cutting devices into the blood vessels. However, these cuts may be replaced by the more easily accomplished cutting pattern formed by the arms 50 and 66 in combination with a cut formed by the first device 30 inserted into the CS when expanded out of the CS. Thus, with the arms 50 and 66 in direct contact with the first cutting device 30 inserted in the CS, the same effect as from the cuts 12 and 14 in FIG. 3 is achieved. The second cutting device 38 inserted into the LIPV is further shown having a cutting arm extending to the LSPV. The third cutting device 54 inserted into the RIPV is further shown having a cutting arm extending to the RSPV. The fourth cutting device 68 inserted into the LSPV is shown having a cutting arm 80 extending to the LAA. The fifth cutting device 82 inserted into the RSPV is shown having a cutting arm extending to the fourth cutting device 68. The cutting arms of the cutting devices 38, 54, 68, 82 may be arranged in any desired combination between the cutting devices 38, 54, 68, 82 forming connections between the cutting devices 38, 54, 68, 82. However, the cutting arms may also be arranged freely, without necessarily having contact to another cutting device.

Figure 19:
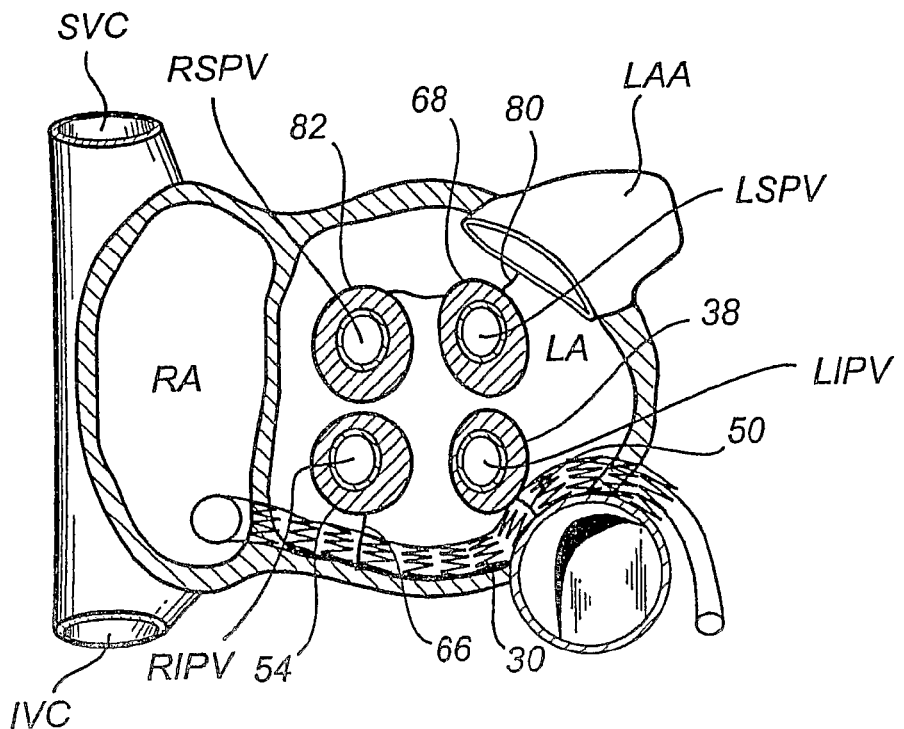

In FIG. 19, the cutting devices shown in FIG. 18 are shown after the change of shape of the devices has occurred. Now, the second, third, fourth and fifth cutting devices 38, 54, 68, 82 have expanded out of the respective PVs and the treated tissue around the orifices of the PVs is shown in shading. Further, the cutting arms have penetrated the heart tissue and have created cutting lines between the PVs, from the LIPV to the mitral valve, from the LSPV to the CS, and from the LSPV to the LAA orifice.

Figure 20:
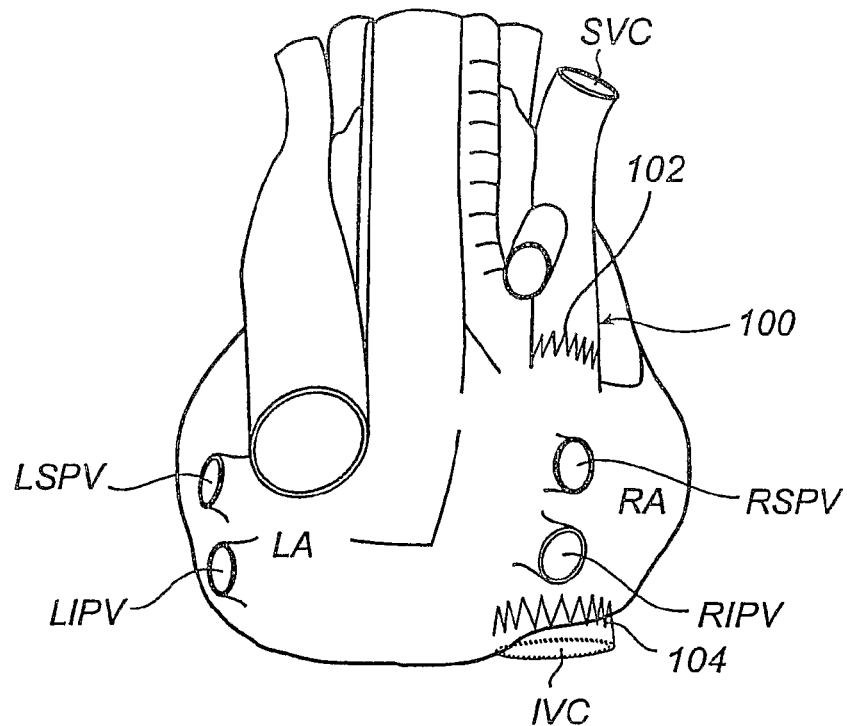
Figure 21:
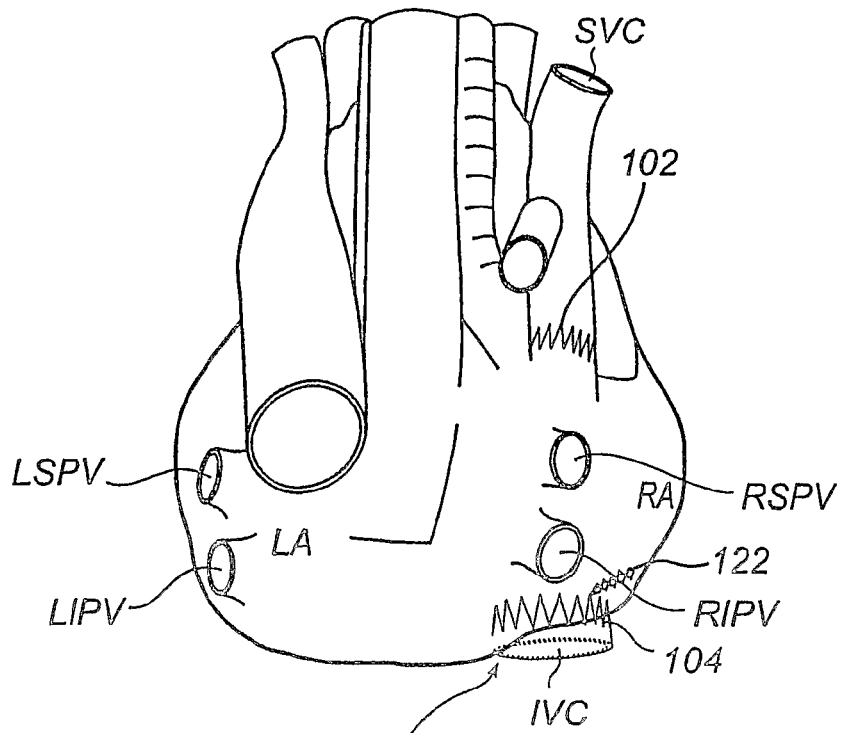
Figure 22:
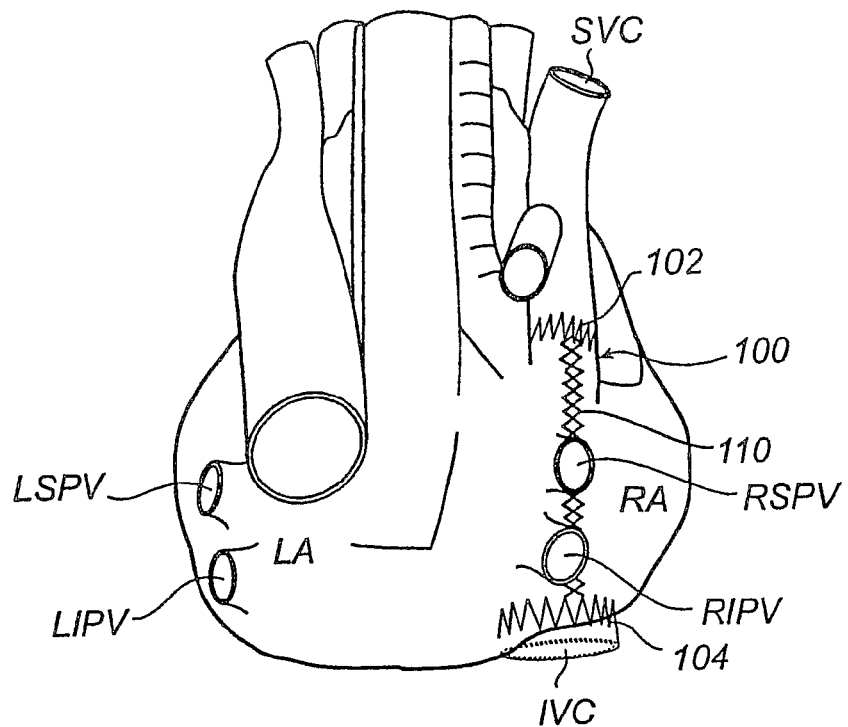
Figure 23:
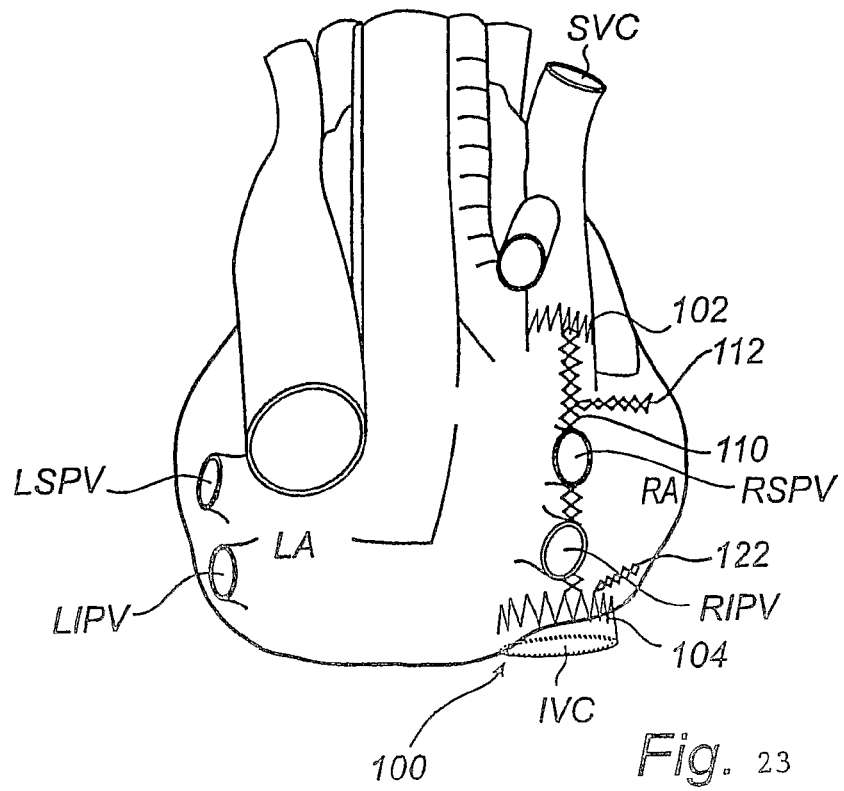

In FIGS. 20-23, different embodiments of the seventh cutting device 100 inserted into the SVC and the IVC is shown. In FIG. 20, the first and second pieces 102, 104 of the seventh cutting device 100 are shown being inserted at the orifices of the SVC and the IVC. The first and second pieces 102, 104 will treat the heart tissue around the orifices of the SVC and the IVC, respectively. In FIG. 21, the second piece 104 is shown comprising a cutting arm 122, which extends from the orifice of the IVC into the orifice of the CS, whereby the cutting arm 122 penetrates heart tissue of the right atrium free wall. In FIG. 22, the seventh cutting device 100 is shown comprising the connecting cutting arm 110, which extends between the first piece 102 inserted into the SVC and the second piece 104 inserted into the IVC. The connecting cutting arm 110 will penetrate heart tissue in the right lateral aspect and the right lateral to posterior aspect of the right atrial wall. In FIG. 23, the seventh cutting device 100 is shown comprising a branch 112 of the connecting cutting arm 110. The branch 112 extends from a point on the connecting cutting arm 110 laterally, creating a vertical cut outwards in the lateral right atrium wall. Alternatively, this branch 112 may be arranged as a further cutting arm extending from the first piece 102 inserted into the SVC.

Figure 24:
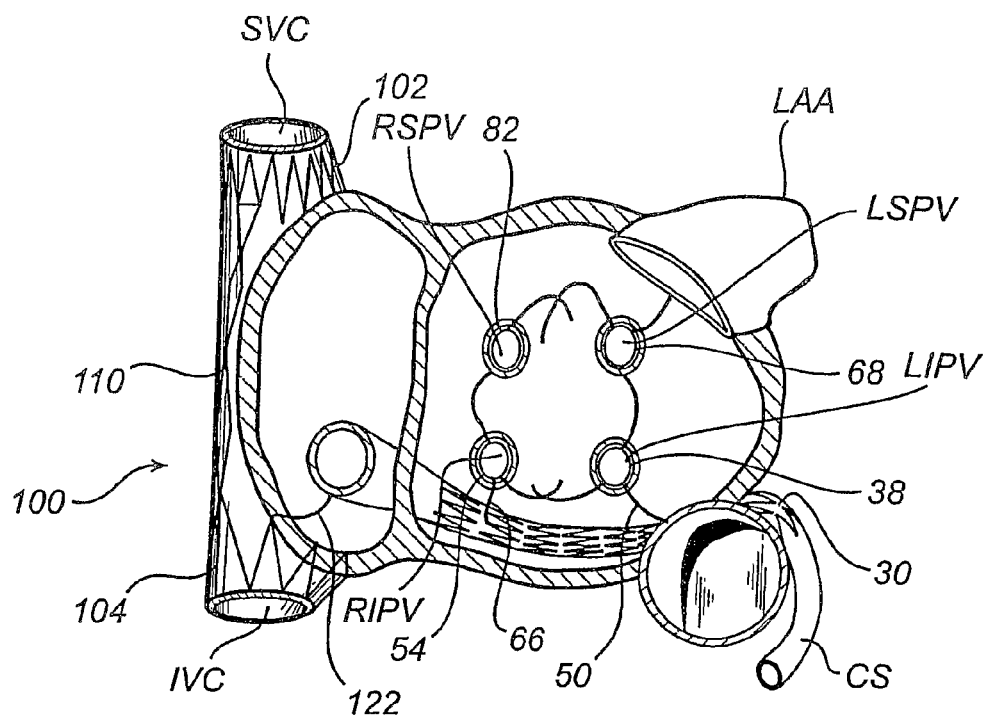
Figure 25:
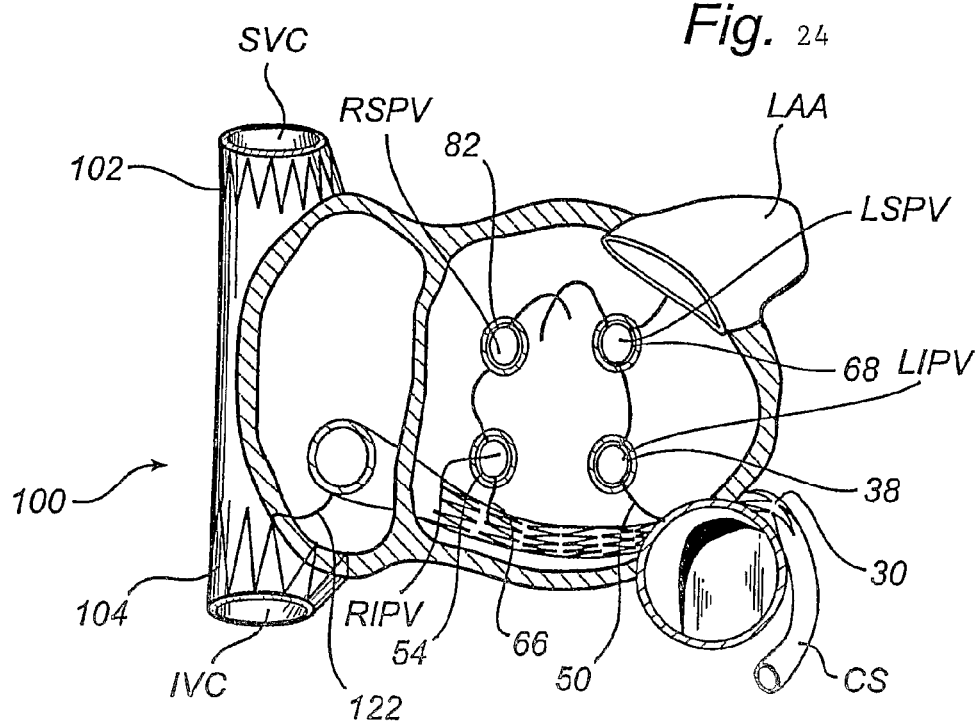

In FIGS. 24-25, the cutting devices according to the present invention are shown inserted into the CS, the PVs and the IVC and the SVC, respectively. The cutting devices are shown in an intermediate state corresponding to the state shown in FIG. 18. Both FIGS. 24 and 25 illustrate cutting arms between the PVs and from the LIPV past the first cutting device 30 in the CS extending to the mitral valve. Thus, the first cutting device 30 inserted in the CS provides a support for the cutting arms extending from the PVs for stabilizing the position of the cutting arms after the change of shape of the cutting devices has been completed. The first cutting device 30 inserted into the CS has, at least partly, an elliptic cross-section enabling the first cutting device 30 to penetrate tissue close to the mitral valve. Also, there is a cutting arm 122 extending from the IVC to the orifice of the CS. In FIG. 24, there is shown the connecting cutting arm 110 between the SVC and the IVC, whereas this connecting cutting arm is not present in FIG. 25. The cutting patterns shown in FIGS. 24 and 25 illustrate cutting patterns that will effectively block propagation of undesired electrical signals in the heart tissue for most patients suffering from disorders to the heart rhythm regulation system. Thus, inserting cutting devices to create these cutting patterns may effectively treat most patients suffering from disorders to the heart rhythm regulation system. However, these cutting patterns do not illustrate treatment of the atrial appendages, as will be shown in FIGS. 26-28. It should be appreciated that the cutting pattern of FIGS. 24 and 25 may be supplemented with this treatment of the atrial appendages. In FIGS. 26-28, there is shown the sixth cutting devices 94 inserted into the LAA and the RAA. As shown in FIGS. 26*a*-*b* in cross-section, the sixth cutting device 94 is inserted at the orifice of the appendage (FIG. 26*a*) and expanded at this position to penetrate through the heart wall (FIG. 26*b*). The sixth cutting device 94 has an elliptic cross-section to fit to the shape of the appendage. In FIG. 27, sixth cutting devices 94 are shown inserted into the LAA and the RAA. The sixth cutting device 94 inserted into the LAA is shown having a cutting arm 124 extending to the LSPV, and the sixth cutting device 94 inserted into the RAA is shown having a cutting arm extending along the lateral right atrium wall. In FIG. 28, the sixth cutting device 94 is shown inserted into the LAA. This sixth cutting 94 device has no cutting arm; instead a fourth cutting device 68 inserted into the LSPV is shown having a cutting arm 80 extending to the LAA. The sixth cutting device 94 inserted into the LAA has a film or membrane 98 covering an end of its tubular part 96 at the LAA orifice. This film or membrane 98 will exclude the LAA from blood contact with the rest of the heart and thereby prohibit migration of thrombus or clot formation from the LAA to, for instance, the brain.

Now, a system for delivery of a cutting device into a desired position in a blood vessel adjacent the heart will be described. Each cutting device may be inserted into its desired position using such a delivery system. The delivery system allows a precise placement of each cutting device into the heart and the big vessels of the body. The delivery system has a restraining device, which keeps the cutting device in its temporary shape. This allows insertion into the blood vessel through catheters having a small bore, making minimal trauma to the patient. The restraining device may be a restraining tube, into which the cutting device is forced in its temporary shape. By cooling the cutting device, in case of a cutting device made of Nitinol, it may be easier to force the cutting device into the restraining tube. Once inserted into the desired position, the cutting device may be pushed out of the restraining tube by means of a piston or the cutting device may be released by retracting the restraining tube from its position over the cutting device. In case of a cutting device made of Nitinol, the cutting device may also be restrained by cooling to prevent it from obtaining a transition temperature trigging the change of shape. Thus, the cutting device may be restrained by cooling during insertion into the desired position and released by suspension of the cooling when inserted at the desired position. In WO 03/022179, such a delivery system is described in more detail.

Now, a method for treating a patient having a disorder to the heart rhythm regulation system will be described. The patient is prepared for operation and operation is performed in an environment allowing visualization of the heart and the attached big vessels using fluoroscopy and ultrasound according to conventional techniques.

Figure 29:
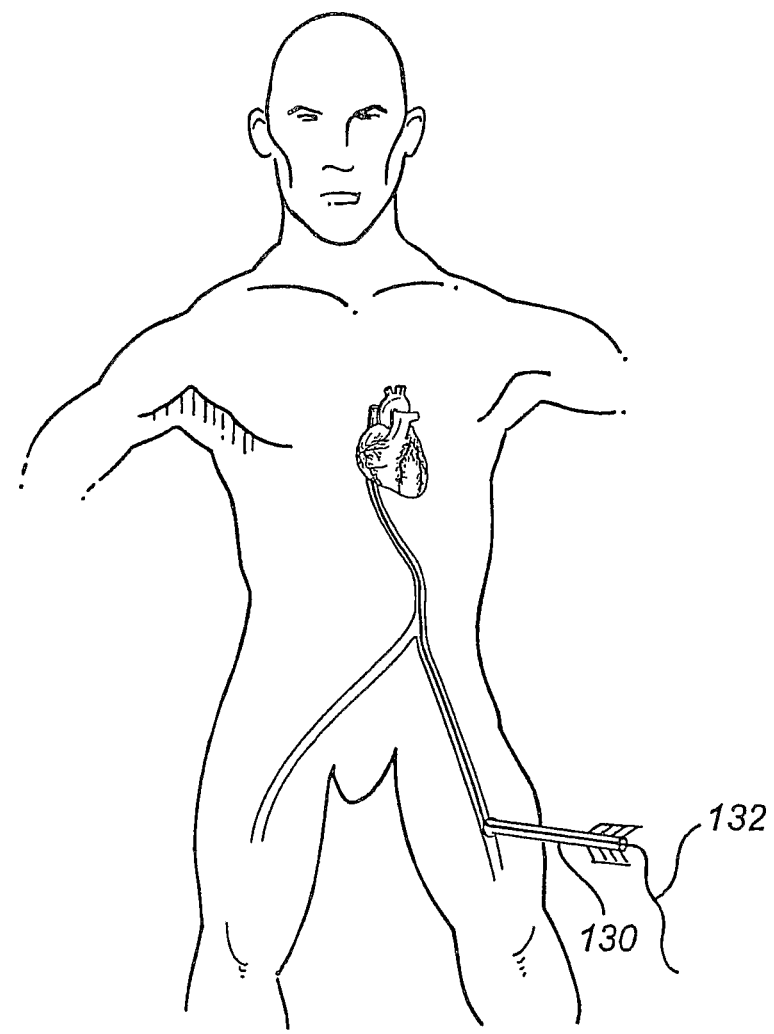
FIGS. 29-31 illustrate three different embodiments of accessing the vascular system.
Figure 30:
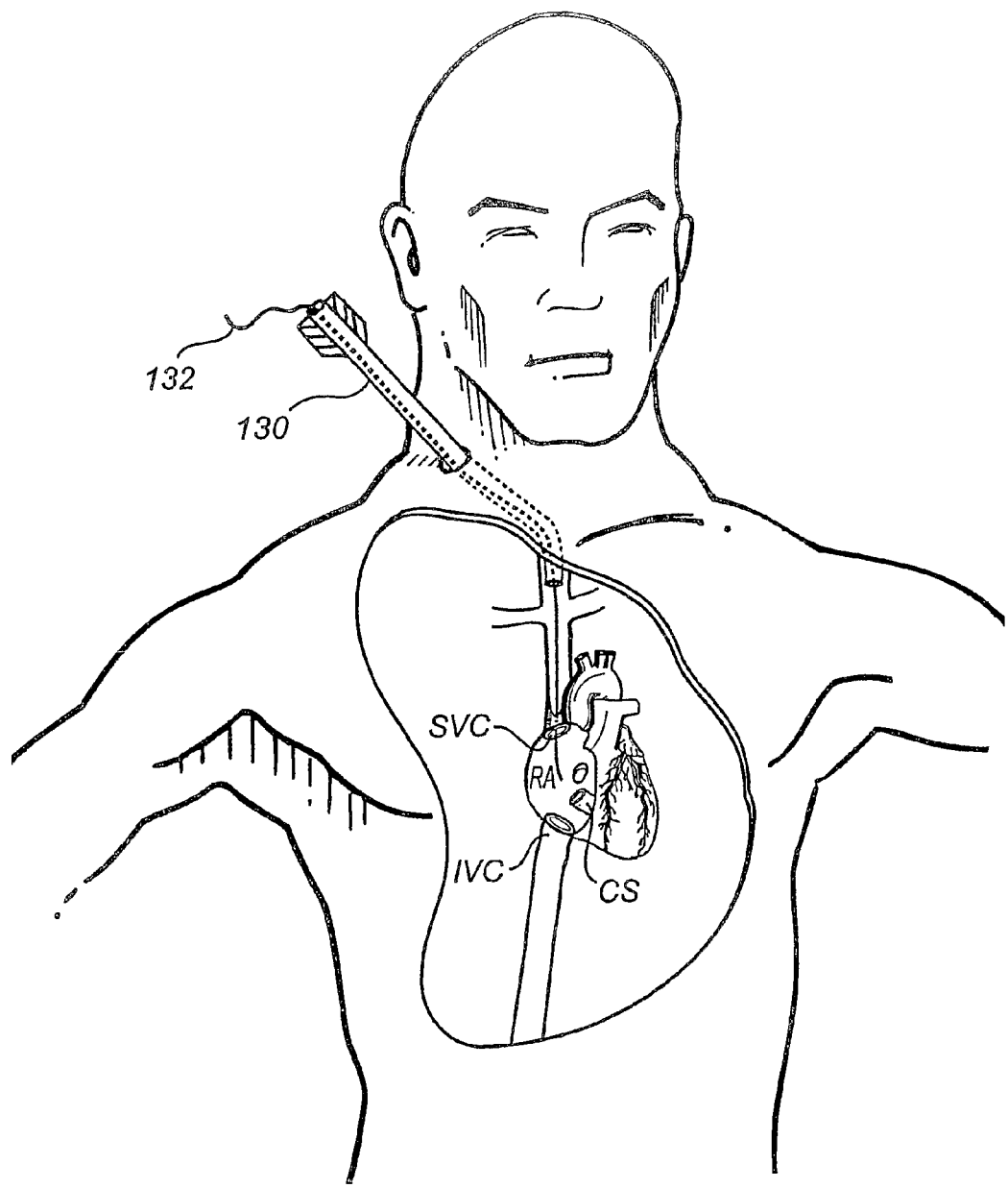
Figure 31:
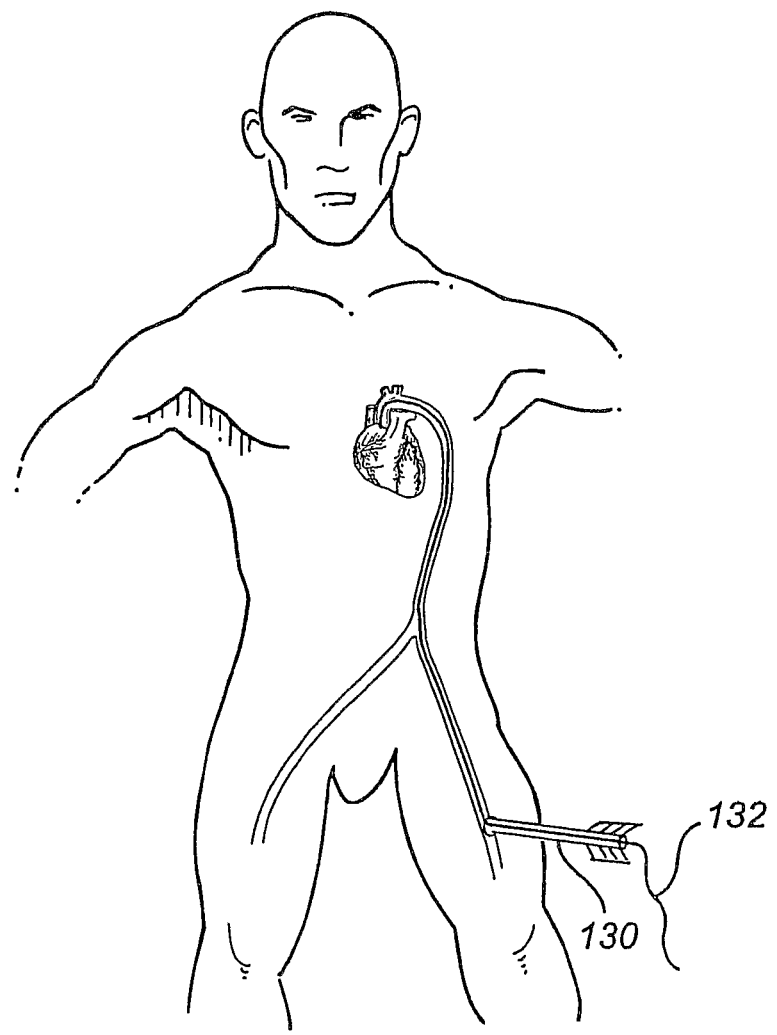
Figure 32:
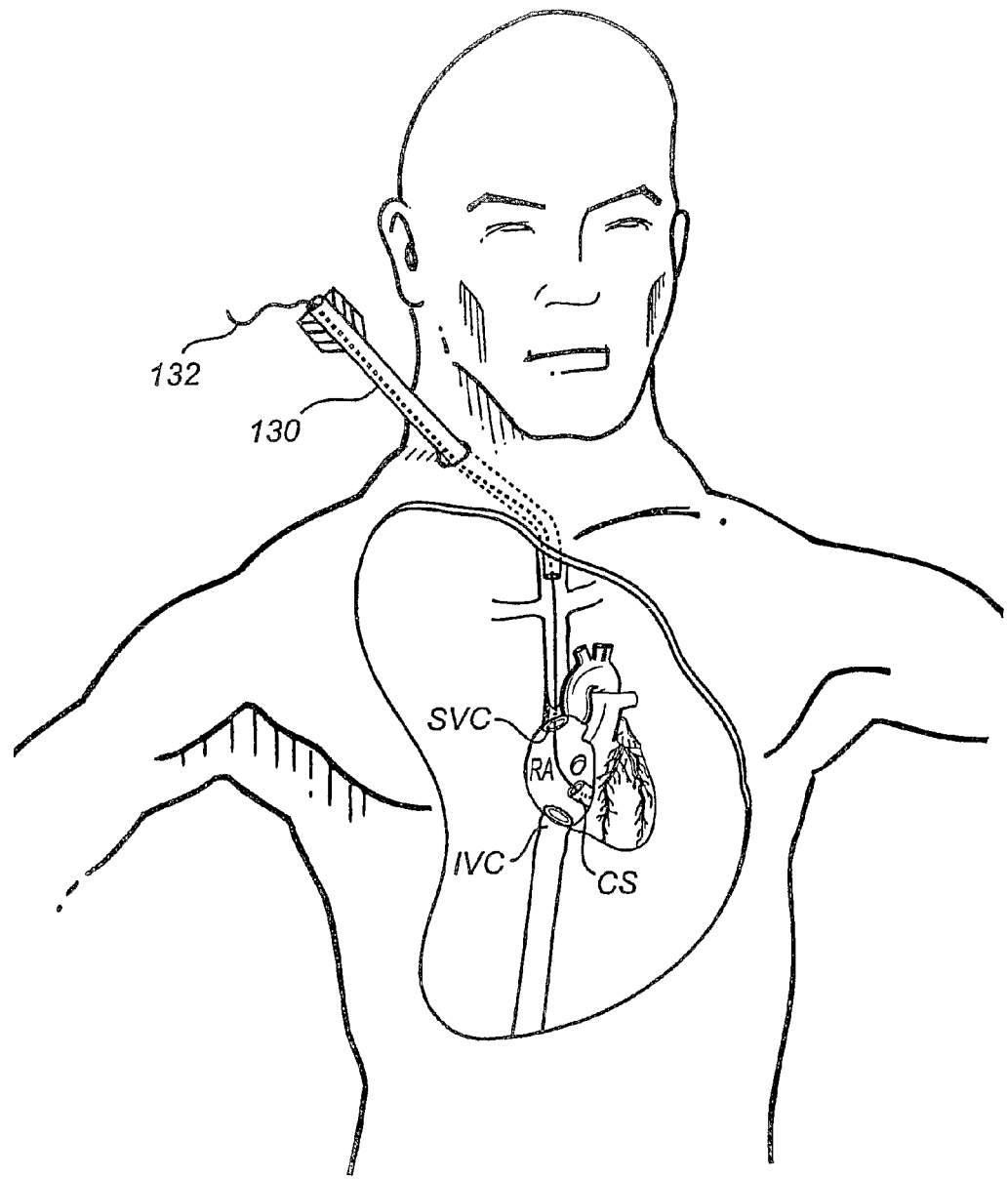
FIG. 32 illustrates a guide wire being inserted into the coronary sinus.

The operation is started by making a puncture of a vein providing an access point to the vascular system of the patient according to conventional techniques. Usually, the femoral vein in the groin, as illustrated in FIG. 29, the subclavian vein on the chest, or the internal or external jugular vein on the neck, as illustrated in FIG. 30, is used. However, other smaller veins may be used instead. Also, in difficult cases when the pulmonary veins cannot be accessed from the vein, arterial access through the femoral artery in the groin may be used, as illustrated in FIG. 31. This method will, however, not be further discussed here. A delivery system is used for inserting the above described cutting devices into blood vessels adjacent the heart. First, an introducer sheath 130 of the delivery system is inserted at the puncture providing an access route into the vascular system. Then, a diagnostic catheter of the delivery system is inserted through the introducer sheath 130 into the vascular system. The diagnostic catheter is manoeuvred through the vascular system into the CS. Next, a guide wire 132 of the delivery system is inserted through a channel of the diagnostic catheter into the CS and all the way to the vein parallel to the left anterior descending artery of the heart, close to the apex of the heart. The guide wire 132 is inserted as far as possible into the vascular system to be firmly positioned. Thereafter, the diagnostic catheter is withdrawn from the patient. The guide wire 132 will then extend from outside the patient into the patient via the access point and inside the patient to the CS, as illustrated in FIG. 32.

Figure 33:
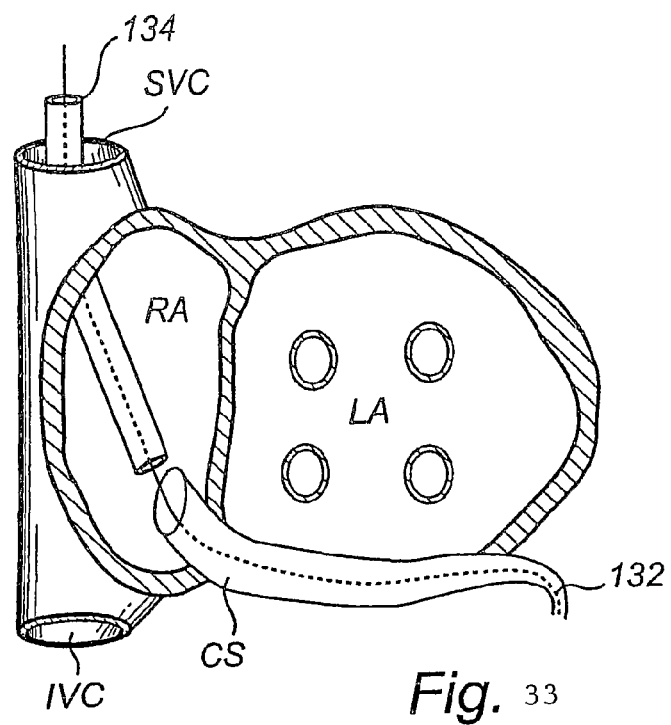
FIG. 33 illustrates a guide wire being inserted into the coronary sinus and a guide catheter being inserted with its tip at the orifice of the coronary sinus.

A guide catheter 134 of the delivery system is now inserted over the guide wire 132 so that the guide catheter 134 is positioned with its tip at the orifice of the CS, as illustrated in FIG. 33. Now, there is a guide wire 132 extending from the outside of the patient and the guide catheter 134, through the guide catheter 134, through the CS, the great cardiac vein and the anterior vein parallel to the LAD all the way to the apex of the heart.

Figure 34:
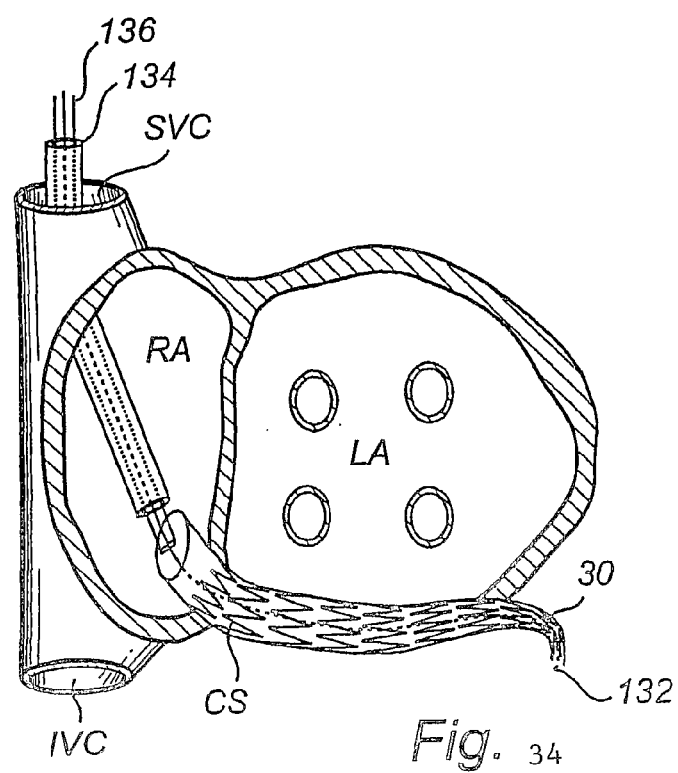
FIG. 34 is a view similar to FIG. 33 showing a first tissue cutting device being inserted into the coronary sinus.

Referring to FIG. 34, a delivery catheter 136 of the delivery system for carrying the first cutting device 30 into the desired position has a guide wire channel throughout its length. The end of the guide wire 132 outside the patient is then inserted into the guide wire channel of the delivery catheter 136, whereby the delivery catheter 136 may be inserted over the guide wire 132 and inside the guide catheter 134 into the CS. The delivery catheter 136 has an inner part providing the guide wire channel and carrying the cutting device at a distal portion. The delivery catheter 136 may further comprise an outer, restraining part, which covers the cutting device and keeps it in a contracted, temporary state. The restraining part may be axially displaceable in relation to the inner part. Thus, the restraining part may be retracted for releasing the cutting device. In this way, the first cutting device 30 is inserted into the CS and may be located in its desired position. A correct position is when the distal end 34 of the first cutting device 30 is positioned within the CS beyond the LIPV next to the CS and the proximal end 36 of the first cutting device 30 is closer to the orifice of the CS than the RIPV. Preferably, the first cutting device 30 extends all the way to the orifice of the CS. Without moving the first cutting device 30 away from its correct position, the first cutting device 30 is released from the delivery catheter. The first cutting device 30 will then immediately expand radially until contact is established with the CS wall, as Illustrated in FIG. 34. Thereafter, the delivery catheter 136 is withdrawn from the patient.

However, the first cutting device 30 is arranged to change shape to assume a shape having much larger diameter than the natural diameter of the CS. Thus, the first cutting device 30 will expand to its designed, permanent shape and the CS wall will not be able to prevent the first cutting device 30 from obtaining its permanent shape. In order to obtain its permanent shape, the first cutting device 30 will therefore penetrate tissue in the path of the change of shape. In this way, the first cutting device 30 will expand to penetrate the heart tissue outside the CS, for instance the left atrium wall. The penetrated tissue will be killed and replaced by fibrous tissue, which is not able to transmit electrical signals. Thus, a block against propagation of undesired electrical signals may be created in this manner.

As an option, the first cutting device 30 may be inserted into the CS in a first separate session of the treatment of a patient. Thus, this first cutting device 30 may be allowed to be well-anchored in the tissue around the CS, before other cutting devices are inserted. This is suitable since some of the other cutting devices are adapted to contact the first cutting device 30 inserted into the CS in order to stabilize and fix their positions. The first cutting device 30 will be well-anchored within a few weeks, typically within three weeks. In this time the first cutting device 30 has penetrated the tissue around the CS and is firmly embedded by the tissue fixing its position. Then, the patient will come back for a second session of the treatment. Thus, a puncture is again made into a vein for allowing access again to the vascular system. However, all the cutting devices may alternatively be inserted during one session.

Figure 35:
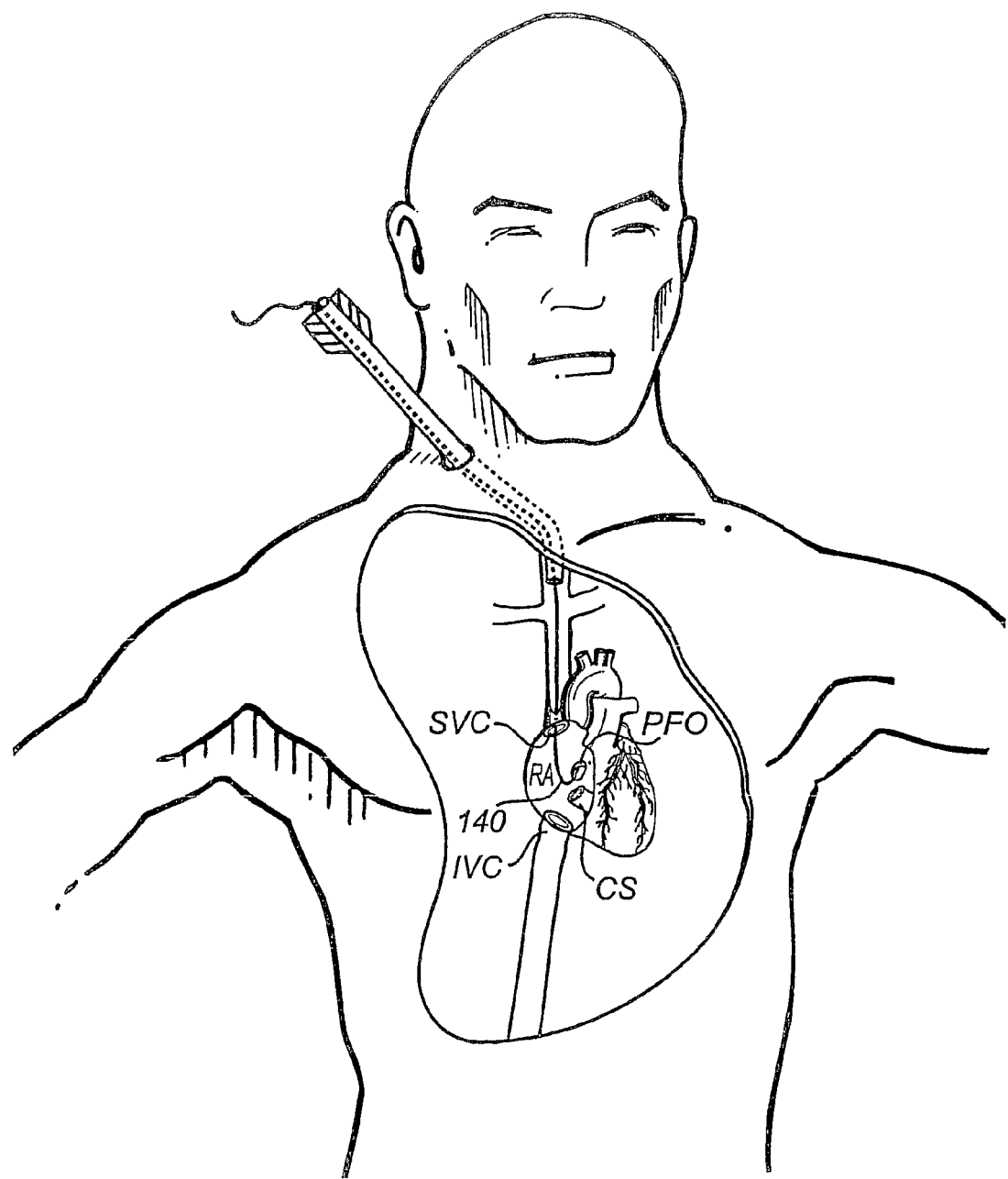
FIGS. 35 and 36 illustrate a guide wire having been inserted into the left atrium.
Figure 36:
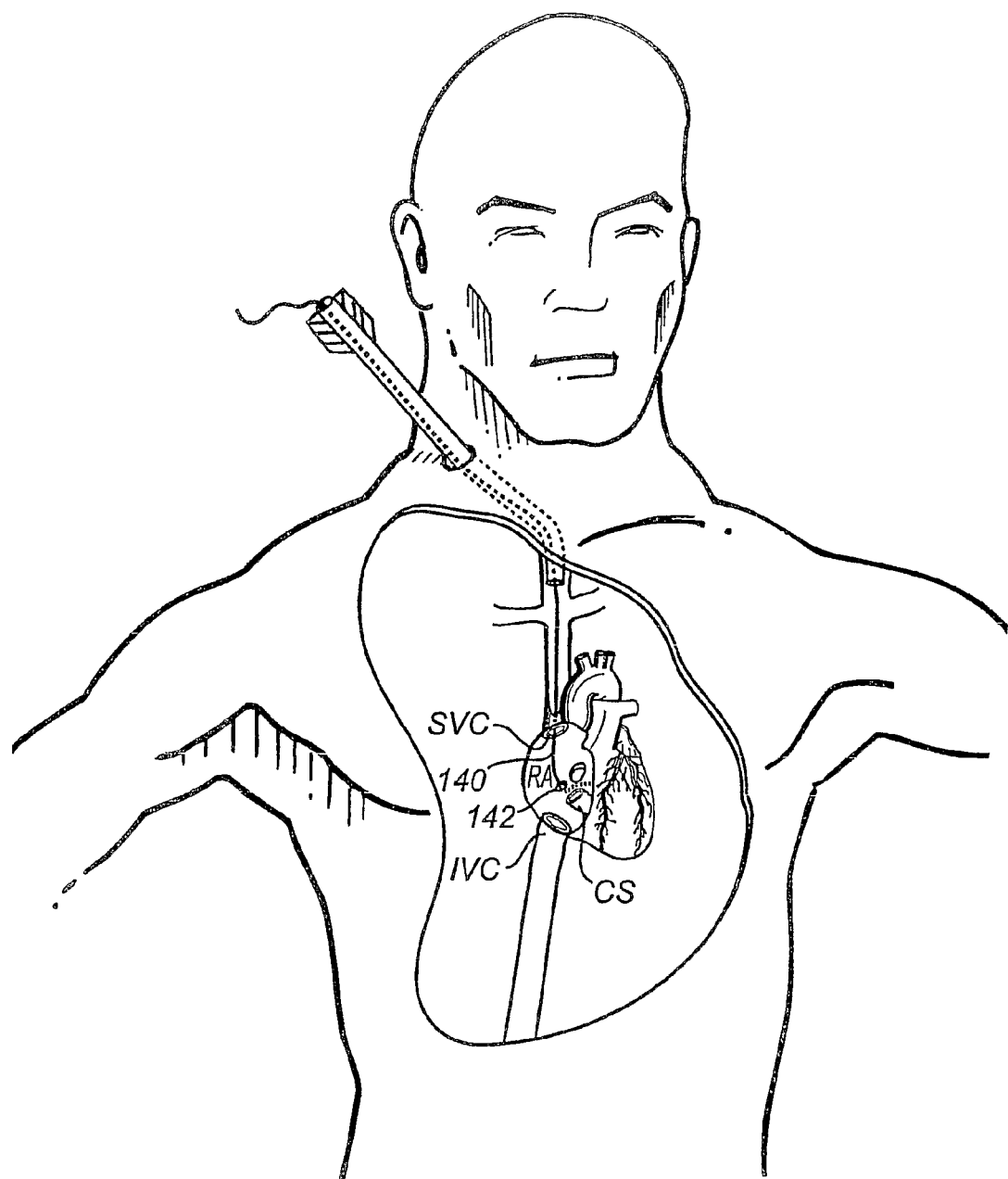

Now, a guide wire 140 is advanced inside a diagnostic catheter into the left atrium (LA), as illustrated in FIGS. 35 and 36. In order to access the LA, the atrial septum between the LA and the right atrium (RA) must be penetrated. If the patient has a patent foramen ovale (PFO, FIG. 35), which is an opening between the LA and the RA that is normally only present during the fetal period in humans, this may be used and enlarged, for instance by means of a balloon catheter (not shown). If no PFO is present (FIG. 36), a small opening 142 must first be created by means of a long flexible needle passed through a diagnostic catheter inside the access vein. Again, the opening 142 in the atrial septum may be enlarged by means of a balloon. Once the needle is inside the LA, the catheter is passed over the needle into the LA and the needle is retracted. A guide wire 140 may now be advanced through the catheter into the LA and further into the LIPV.

Figure 37:
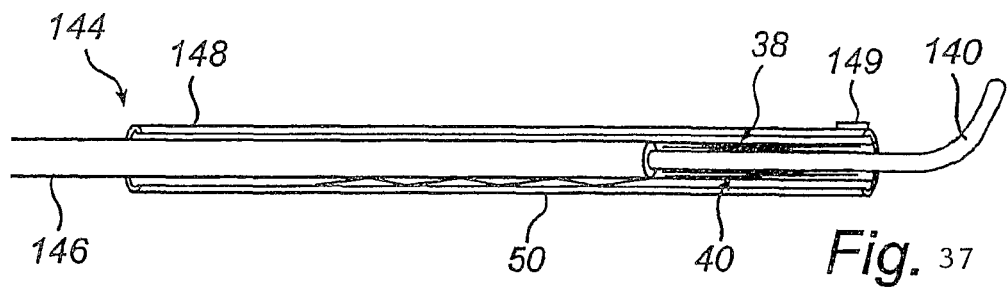
FIGS. 37-39 illustrate the carrying and deployment of a tissue cutting device by means of a delivery catheter.
Figure 38:
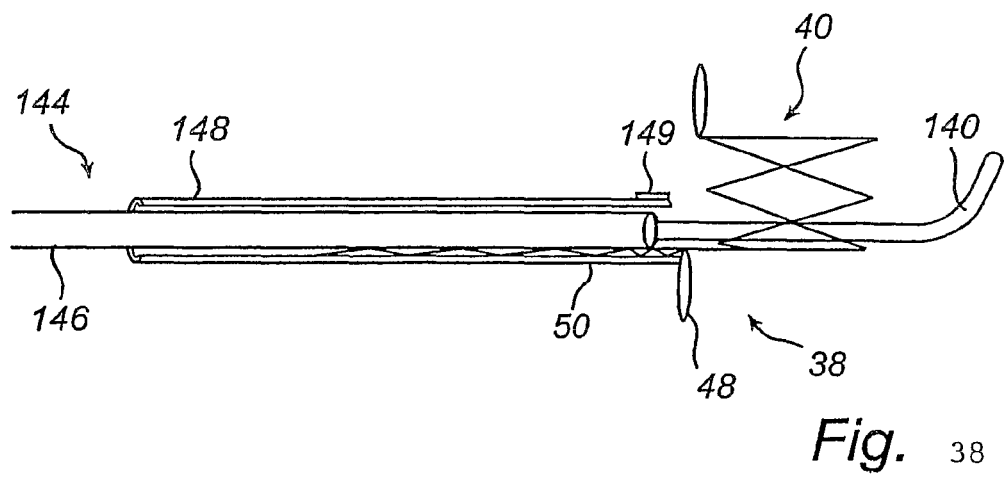
Figure 39:
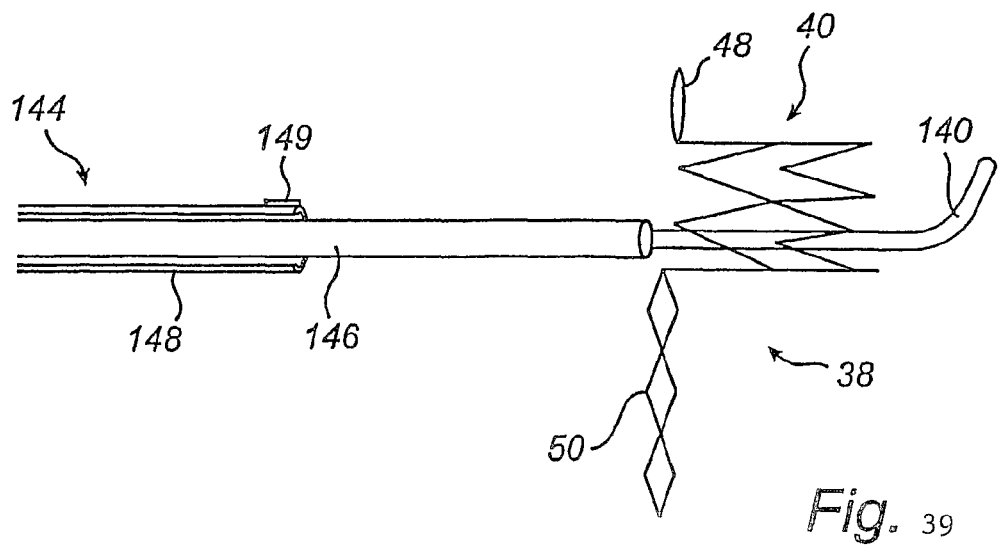

Referring now to FIGS. 37-39, the release of a cutting device will be generally described. Thus, having now placed the guide wire 140, the second cutting device 38 may be inserted to its desired position using a guide catheter extending to the LIPV orifice and a delivery catheter 144, as illustrated in FIG. 37, in a similar manner as for the insertion of the first cutting device 30. The delivery catheter 144 has an inner part 146 providing the guide wire channel. The tubular part 40 of the second cutting device 38 is arranged in front of the inner part 146 such that the inner part 146 of the delivery catheter 144 pushes the tubular part 40 in front of it. The delivery catheter 144 may further comprise an outer, restraining part 148, which covers the cutting device and keeps it in a contracted, temporary state. The restraining part 148 may be axially displaceable in relation to the inner part 146. Thus, the restraining part 148 may be retracted for releasing the cutting device 38. The delivery catheter 144 has a marker on the catheter outside the patient, as well as a x-ray marker 149 visible on the fluoroscopy, indicating securely the orientation of the cutting arm 50 of the second cutting device 38. The second cutting device 38 is now rotated into a position where it will change shape in such a way that the cutting arm 50 will extend to contact and be supported by the first cutting device 30, which has been inserted previously. The second cutting device 38 is advanced into a position where the atrial end 48 of the second cutting device 38 is still outside the LIPV orifice. When the correct position of the second cutting device 38 is confirmed by means of fluoroscopy and/or ultrasound, the distal end of the second cutting device 38 is released from the delivery catheter far inside the PV, whereby the distal end will expand radially to fix the position of the second cutting device 38. Next, a mid portion of the second cutting device 38 and the atrial end 48 is released, as illustrated in FIG. 38. Now, the cutting arm 50 is released, as illustrated in FIG. 39, and allowed to assume its radial extension from the tubular part 40, whereby it will penetrate the heart wall to contact the first cutting device 30.

Now, the guide wire 140 is retracted into the LA. The diagnostic catheter is inserted again and guided into the RIPV, whereby the guide wire 140 may be inserted into the RIPV. Thereafter, the diagnostic catheter is withdrawn from the patient. Then, the third cutting device 54 is inserted using a guide catheter extending to the RIPV orifice and a delivery catheter 144 in a manner similar to the insertion of the second cutting device 38. Thus, the orientation of the cutting arm 66 of the third cutting device 54 is determined in the same manner as for the second cutting device 38. Having correctly positioned the third cutting device 54, the tubular part 56, the atrial end 64 and the cutting arm 66 of the third cutting device 54 are released in a manner similar to the release of the second cutting device 38. Now, the cutting arm 66 is released and allowed to assume its radial extension from the tubular part 56, whereby it will penetrate the heart wall to contact the first cutting device 30.

Figure 40:
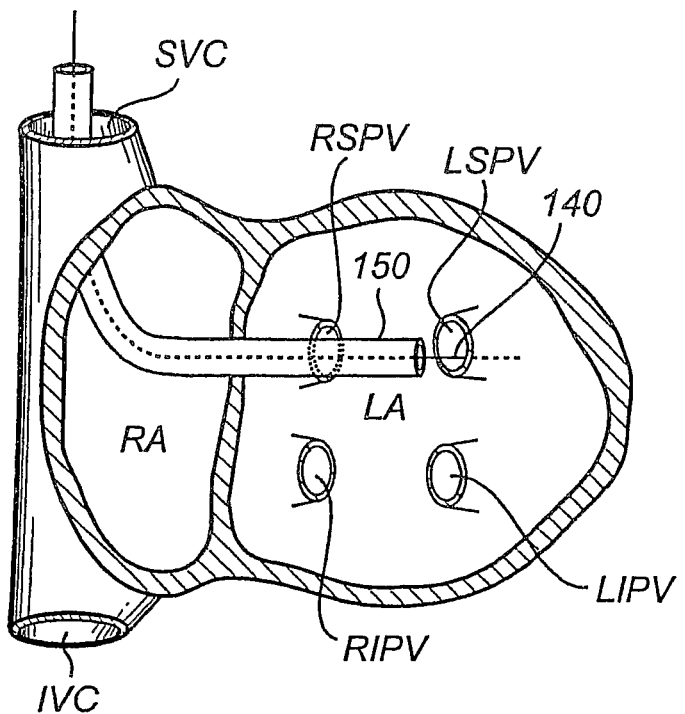
FIGS. 40-42 illustrate the deployment of a tissue cutting device in the left superior pulmonary vein.
Figure 41:
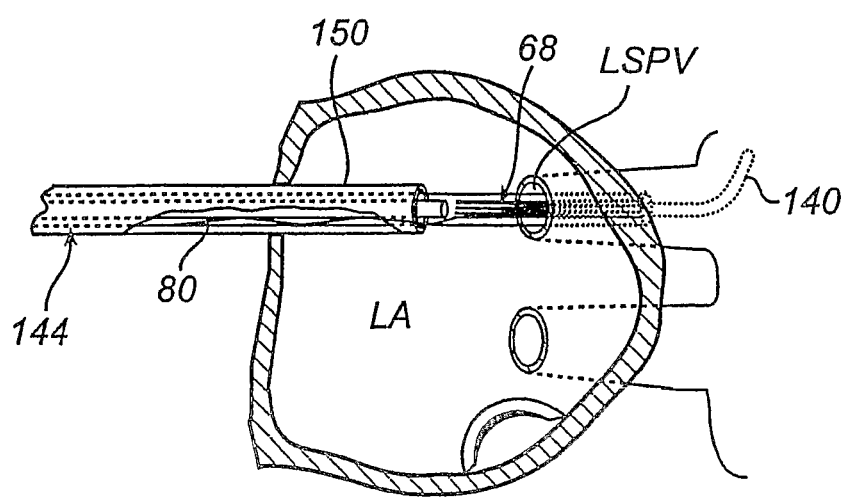
Figure 42:
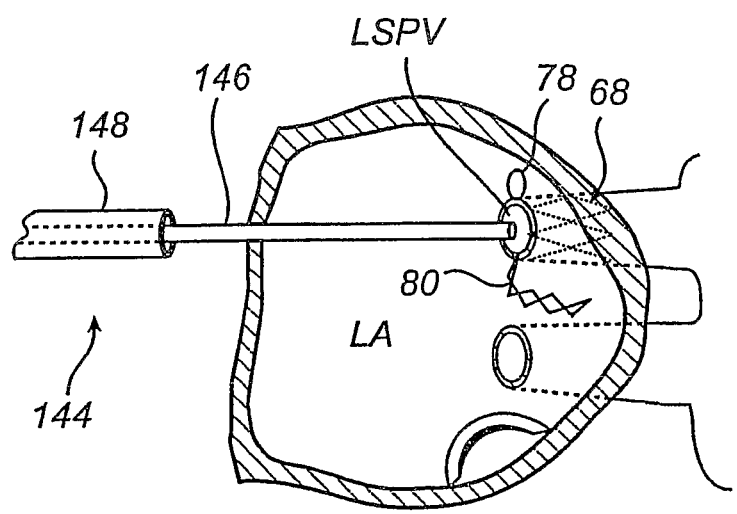

Thereafter, the guide wire 140 is again retracted into the LA and inserted into the LSPV, as illustrated in FIG. 40. Then, the fourth cutting device 68 is inserted using a guide catheter 150 extending to the LSPV orifice and a delivery catheter 144, as illustrated in FIG. 41, in a manner similar to the insertion of the second and third cutting devices 38, 54. Thus, the orientation of the cutting arm 80 of the fourth cutting device 68 is determined in the same manner as for the second and third cutting devices 38, 54. The fourth cutting device 68 may have two cutting arms, which are adapted to extend towards the second cutting device 38 and towards the LAA. Having correctly positioned the fourth cutting device 68, the tubular part 70, the atrial end 78 and the one or two cutting arms 80 of the fourth cutting device 68 are released in a manner similar to the release of the second and third cutting devices 38, 54, as further illustrated in FIG. 42. Now, the cutting arms are released and allowed to assume their radial extension from the tubular part 70, whereby they will penetrate the heart wall to contact the second cutting device 38 or extend to the orifice of the LAA, respectively.

Again, the guide wire 140 is retracted into the LA and inserted into the RSPV. Then, the fifth cutting device 82 is inserted using a guide catheter 150 extending to the RSPV orifice and a delivery catheter 144 in a manner similar to the insertion of the second, third and fourth cutting devices 38, 54, 68. Usually, the fifth cutting device 82 has no cutting arm and therefore only the axial position of the fifth cutting device 82 needs to be determined. Having correctly positioned the fifth cutting device 82, the tubular part 84, and the atrial end 92 of the fifth cutting device 82 are released in a manner similar to the release of the second, third, and fourth cutting devices 38, 54, 68.

Once again, the guide wire 140 is retracted into the LA and now inserted into the LAA. Then, the sixth cutting device 94 is inserted using a guide catheter 150 extending to the LAA orifice and a delivery catheter 144 in a manner similar to the insertion of the other cutting devices. The sixth cutting device 94 is advanced into a position where the entire sixth cutting device 94 is inside the LAA, and a proximal end of the sixth cutting device 94 is adjacent to the LAA orifice. The delivery catheter 144 has a marker on the catheter outside the patient, as well as a x-ray marker 149 visible on the fluoroscopy, indicating securely the orientation of the sixth cutting device 94 such that the elliptic shape of the sixth cutting device 94 may be oriented in correspondence to the elliptic shape of the LAA. When the correct position of the sixth cutting device 94 is confirmed by means of fluoroscopy, a distal end of the sixth cutting device 94 is released from the delivery system far inside the LAA, whereby the distal end will expand radially towards the wall of the LAA to fix the position of the sixth cutting device 94. Next, a mid portion of the sixth cutting device 94 and a proximal end are released. Now, the sixth cutting device 94 is allowed to change its shape to cut through the heart wall of the LAA.

Now, the guide wire 140 is retracted from the LA into the RA and inserted into the RAA. Then, another sixth cutting device 94 is inserted using a guide catheter 150 extending to the RAA orifice and a delivery catheter 144 in a manner similar to the insertion of the other cutting devices. The other sixth cutting device 94 is advanced into a position where the entire sixth cutting device 94 is inside the RAA, and a proximal end of the sixth cutting device 94 is adjacent to the RAA orifice. The position of the sixth cutting device 94 is determined in a manner similar to the positioning of the sixth cutting device 94 inserted into the LAA. When the correct position of the sixth cutting device 94 is confirmed, the sixth cutting device 94 inserted into the RAA is released in a manner similar to the release of the sixth cutting device 94 inserted into the LAA. Now, the sixth cutting device 94 is allowed to change its shape to cut through the heart wall of the RAA.

Figure 43:
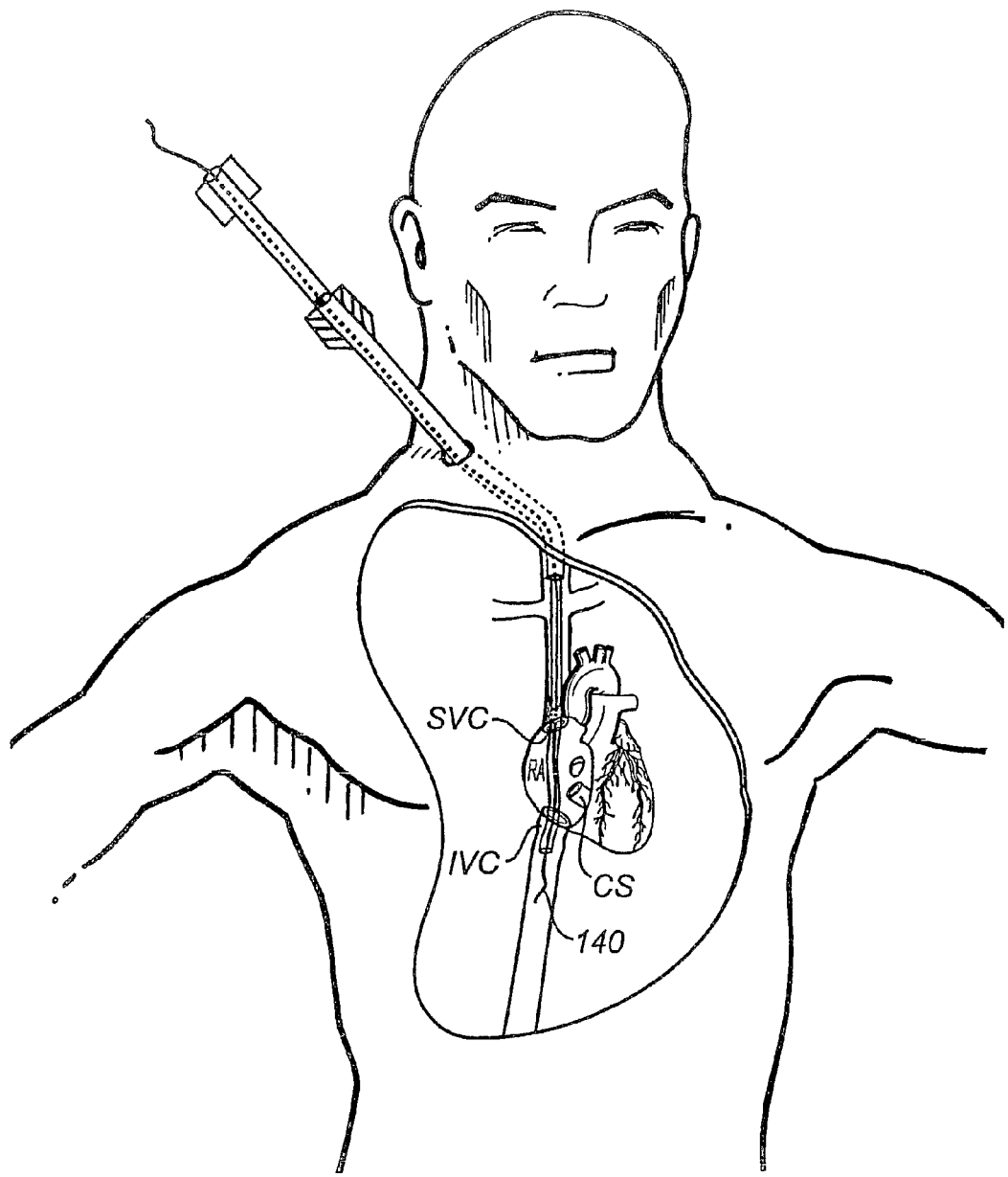
FIGS. 43-46 illustrate the insertion of a tissue cutting device into the inferior and superior vena cava.
Figure 44:
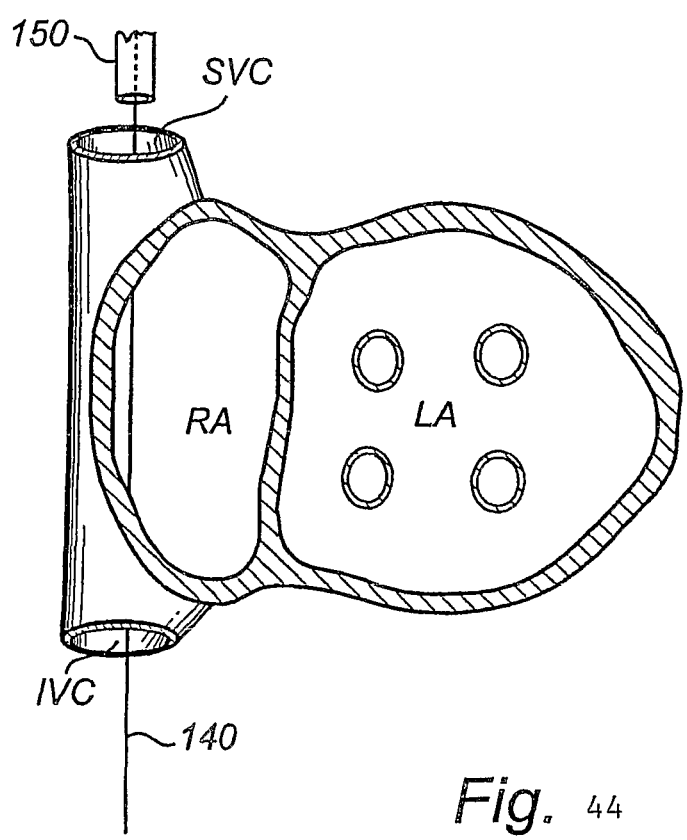
Figure 45:
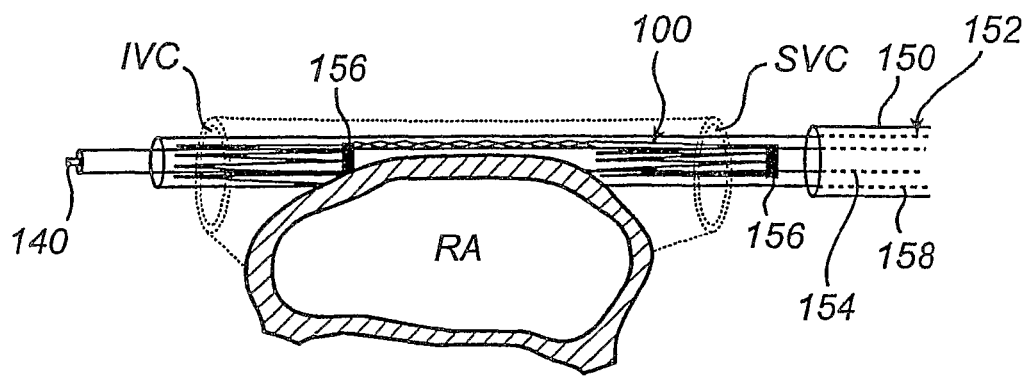
Figure 46:
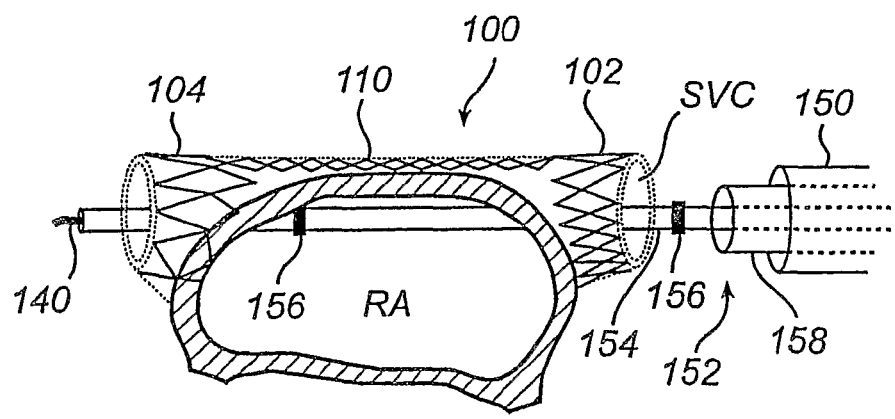

Next, the guide wire 140 is retracted from the RAA into the RA. If the access point to the vascular system was created in the upper part of the body, the guide wire 140 extends through the SVC into the RA. Then, the guide wire 140 is further inserted into the IVC, as illustrated in FIG. 43. On the other hand, if the access point to the vascular system was created in the lower part of the body, the guide wire 140 extends through the IVC into the RA. Then, the guide wire 140 is further inserted into the SVC. Thereafter, the seventh cutting device 100 is inserted using a guide catheter 150, as illustrated in FIG. 44, and a delivery catheter 144 in a manner similar to the insertion of the other cutting devices. The seventh cutting device 100 is placed in position in the IVC, SVC and the RA, as illustrated in FIG. 45. The delivery catheter 152 carries the seventh cutting device 100 on the inner part 154 of the catheter 152. The inner part 154 comprises stops 156, which prevent the seventh cutting device 100 from being axially displaced from the inner part 154 during insertion of the device. Again, the cutting device 100 is kept in a contracted, temporary state by means of a restraining part 158. The correct orientation of the seventh cutting device 100 is obtained in a manner similar to the positioning of the second, third and fourth cutting devices 38, 54, 68. The seventh cutting device 100 has now been rotated into a position where it will change shape in such a way that its cutting arm or cutting arms 122 will extend in intended directions. Thus, the seventh cutting device 100 may comprise a cutting arm 122 that extends towards the orifice of the CS and/or a branch 112 that extends from the connecting cutting arm 110 of the seventh cutting device 100 towards the lateral wall of the RA. When the correct position of the seventh cutting device 100 is confirmed by means of fluoroscopy, a distal end of the seventh cutting device 100 in the delivery catheter 152 is released from the delivery catheter 152 in the IVC or SVC, depending on where the distal end of the delivery catheter is placed. Thereafter, the connecting cutting arm 110 is released and finally a proximal end of the seventh cutting device 100 is released, as illustrated in FIG. 46.

Now, the guide wire 140 and the delivery catheter 152 is retracted outside the patient, since all parts of the treatment kit have been implanted.

On special indication, for instance when it is difficult to place the guide wire inside the PVs, an arterial access may be used instead. The insertion technique is identical, except that the access to the vascular system is achieved by puncture of an artery and that the cutting devices are delivered through the arterial system instead of through the venous system. After puncture of the artery, a catheter is advanced through the aorta and passed by the aortic valve into the left ventricle and finally into the LA. The guide wire is advanced into the desired PV and the insertion of the cutting device may then be achieved in the manner described above.

Figure 47:
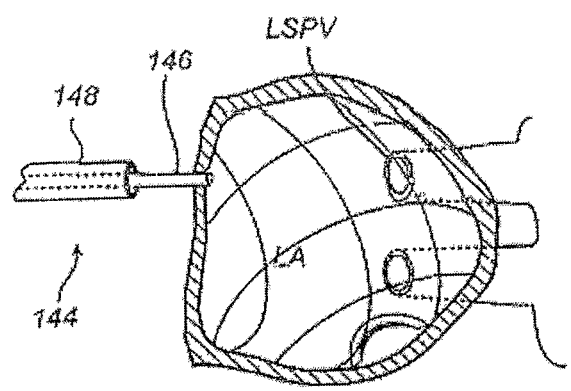
FIGS. 47a-47b illustrate the deployment of a tissue cutting device according to FIG. 14 in the left atrium.
Figure 47:
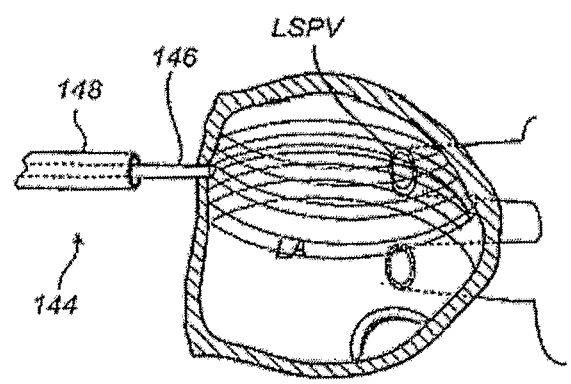

Referring now to FIGS. 47*a* and *b*, the release of a cutting device, according to FIG. 14, into the left atrium will be generally described. Thus, having now placed the guide wire 140, the cutting device according to FIG. 14 may be inserted to its desired position using a guide catheter extending to the LA and a delivery catheter 114, as illustrated in FIG. 37, in a similar manner as for the insertion of the first cutting device 30. The delivery catheter 144 has an inner part 146 providing the guide wire channel. The guiding catheter and the delivery catheter are advanced well into the LA so that when releasing the device into the LA the device gets contact with the wall furthest away, the guiding catheter is retracted into the RA and the restraining catheter is retracted towards the atrial septum causing the device to be released into the LA. The catheters and the guide wire are retracted to outside the patient.

Figure 48A:
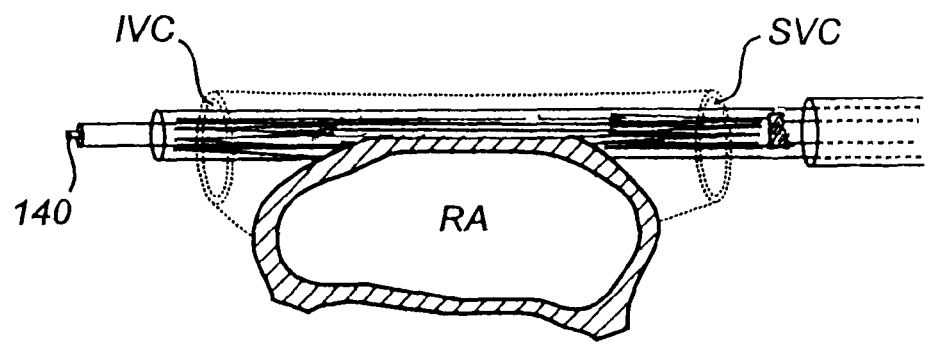
FIGS. 48a-48b illustrate the deployment of a tissue cutting device according to FIG. 14 in the right atrium.
Figure 48B:
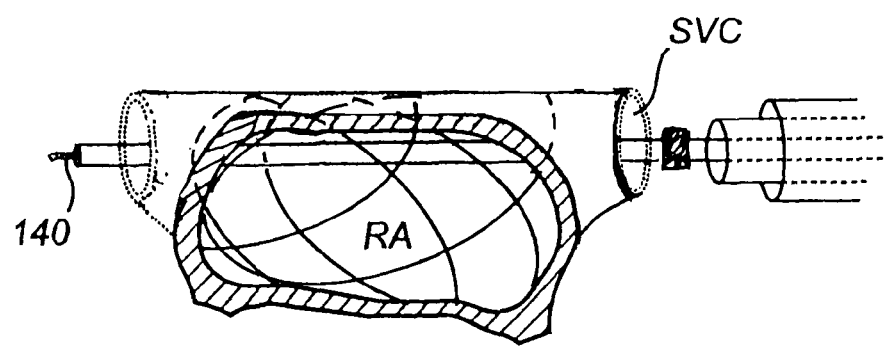

Now a release of the device in the RA is described. The guide wire is advanced into the IVC if the approach is from the neck and into the SVC if the approach is from the groin, according to FIGS. 48*a* and *b*. The delivery catheter is advanced to the most distant point where the atrial device is to be deploid, the restraining catheter is retracted towards the SVC or IVC respectively, causing the device to be released into the RA, according to FIG. 48*b*. The catheters and the guide wire are retracted to outside the patient.

Figure 49:
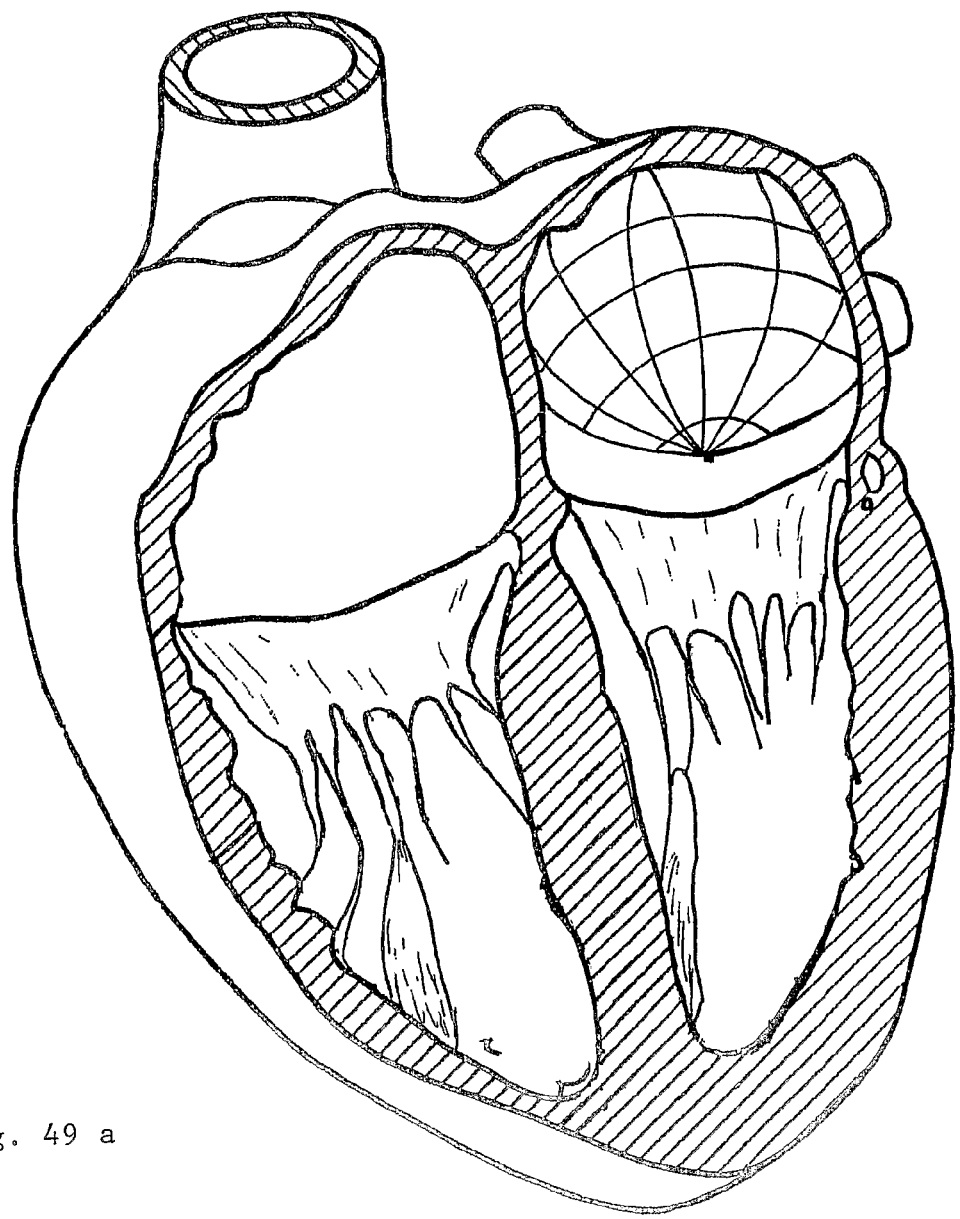
FIGS. 49a-49b illustrate a tissue lesion creating cutting device according to FIG. 14a located in the left atrium.
Figure 49:
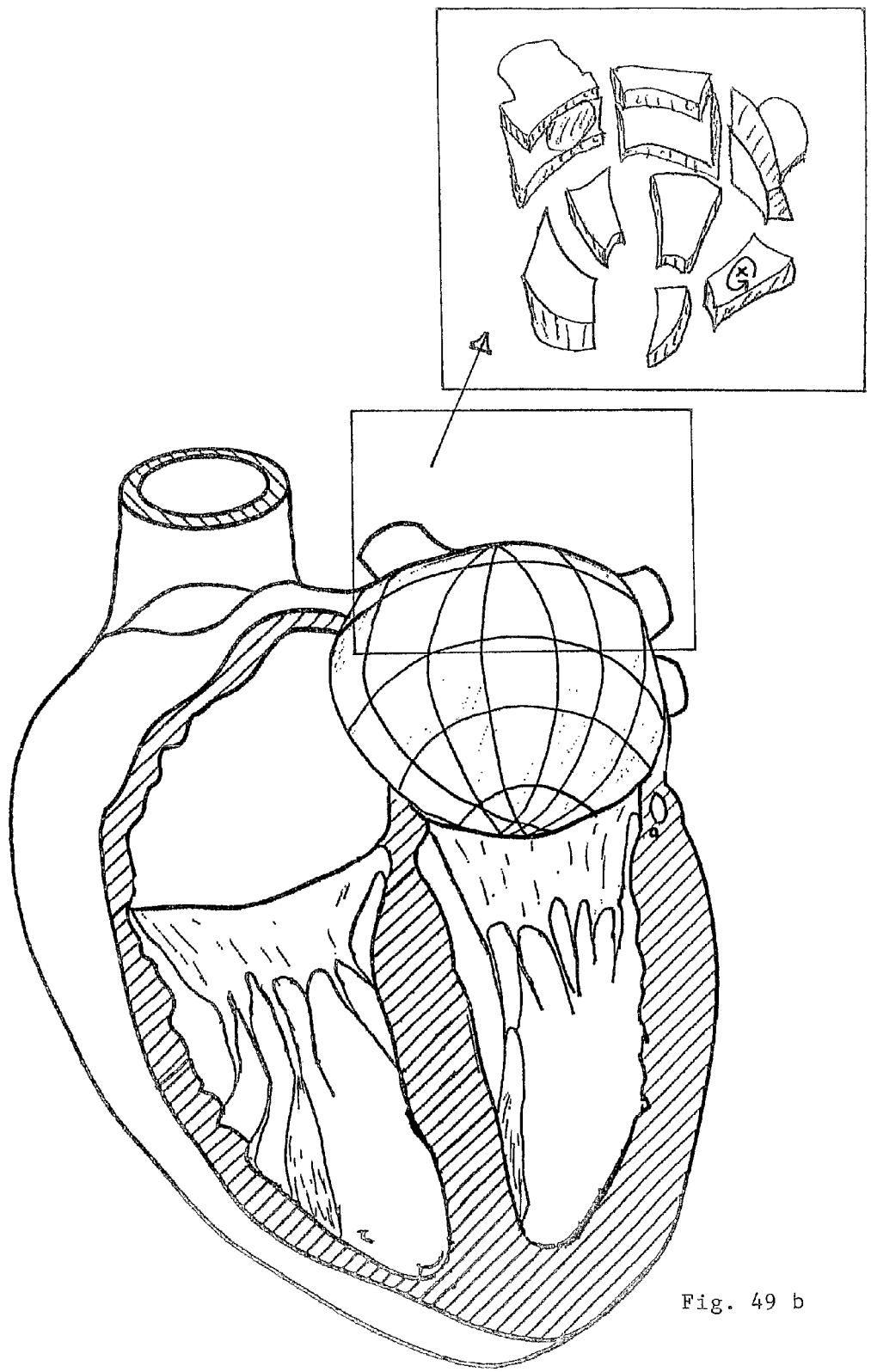

FIG. 49*a* shows the cutting device according to FIG. 14*a* positioned in the RA, and FIG. 49*b* shows the same cutting device in the permanent, expanded shape, i.e. when the wall of the RA has been cut. The cutting devices according to the present invention have now been released such that they may change their shapes to obtain their permanent shapes. During the change of shape, each cutting device will penetrate heart tissue in the path of the change of shape. Thus, the cutting devices will now create the cutting pattern intended for forming blocks against propagation of undesired electrical signals in the heart. After the cutting devices have made their change of shape, the needed effect of the cutting devices on the heart tissue is completed. Thus, if the cutting devices are made of resorbable shape memory polymers, the cutting devices will be resorbed a time after termination of the cutting procedure. This time for resorption can be set by determination of the different ingredients of polymers and also by means of external altering, for instance by means of x-ray radiation, ultrasound, electron beams, or light of a defined wavelength, setting the time of the polymers to be resorbed. However, the cutting devices may also be left in the body after the change of shape, or only some of the cutting devices may be resorbed.

Hereinafter, some potential uses of the present invention are described:

A method for treatment of disorders in the heart rhythm regulation system, said method comprising:

inserting a tissue cutting device through the vascular system to a desired position in a body vessel, and providing a change of shape of the tissue cutting device at said desired position to penetrate heart tissue adjacent said body vessel.

The method according to above, wherein said tissue cutting device is inserted into a desired position in the coronary sinus, in any of the pulmonary veins, in the superior vena cave, in the inferior vena cava, or in the left or right atrial appendage. The method according to above, further comprising inserting another tissue cutting device to another of the desired positions.

The method according to above, further comprising inserting a tissue cutting device into each of the desired positions.

The method according to above, further comprising restraining the tissue cutting device in an insertion shape during the inserting of the tissue cutting device.

The method according to above, wherein the restraining comprises keeping the tissue cutting device inside a tube.

The method according to above, wherein the restraining comprises cooling the tissue cutting device.

The method according to above, further comprising releasing a restrain on the tissue cutting device when it has been inserted into the desired position for allowing said change of the shape of the tissue cutting device.

It should be emphasized that the preferred embodiments described herein is in no way limiting and that many alternative embodiments are possible within the scope of protection defined by the appended claims.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A tissue cutting device configured to reduce undesired signal transmission in a heart tissue in order to treat arrhythmia, wherein:
    the device is structured and arranged to be inserted in a temporary delivery shape through the vascular system and at least partly be positioned into said atrium that is intended to be treated and to be subsequently subjected to a change of shape, from said temporary delivery shape via an expanded delivered shape to a further expanded shape, extending at least beyond an outer surface of said atrial tissue,
    said tissue cutting device is configured to create cutting action for cutting of said heart tissue including said atrium, and wherein said tissue cutting device is structured and arranged to penetrate a wall of said heart tissue by said cutting action, in such a manner that a cut of said tissue created by said cutting action is continuously replaced by scar tissue that does not conduct electrical signals to isolate ectopic sites of said heart tissue causing said arrhythmia,
    the device is combined with a tubular part structured and arranged to be inserted in a temporary delivery shape through the vascular system into a body vessel adjacent to the heart, and to be subsequently subjected to a change of shape, from said temporary delivery shape via an expanded delivered shape to a further expanded shape, extending at least beyond an outer surface of a tissue surrounding said body vessel, in order to create said cutting action configured for cutting said heart tissue and/or a cutting action configured for cutting said tissue surrounding said body vessel,
    the tubular part of said device comprises a plurality of segments connected to each other in a longitudinal direction of said tubular part of said device,
    a first segment of said plurality of segments has a dimension in a direction perpendicular to said longitudinal direction of said tubular part of said device that is larger than that dimension of a second segment thereof, at least in said expanded delivered shape,
    said device further comprises at least one cutting arm being structured and arranged to initially extend substantially perpendicular to said longitudinal direction from the tubular part of said tissue cutting device in order to be inserted into a heart atrium wall and said cutting arm being structured and arranged to change shape to extend radially from the tubular part of said tissue cutting device.

2. The device according to claim 1, wherein the device is of an at least partly spherical shape.

3. The device according to claim 1, wherein the device is made out of at least one thread or wire.

4. The device according to claim 3, wherein the device is made from a plurality of wires, and wherein the wires are interconnected or braided to each other.

5. The device according to claim 1, wherein the device is formed in a net-like pattern to a shape that is arranged to encompass at least a portion of said atrium that it is intended to treat before cutting through a wall of said atrium.

6. The device according to claim 5, wherein the net-like pattern forms a spherical form encompassing a substantial part of said atrium, an ellipsoidal segment that is arranged to encompass a substantial part of said atrium, a cup-shape, or a globulus arranged and configured to be placed inside said atrium.

7. The device according to claim 1, wherein:
    at least a part of the device, in the further expanded shape, has a form that is the same as at least a part of the inner surface of said atrium but is larger than the atrium,
    the device expands from the expanded delivered shape inside said atrium, through the entire wall of said atrium, to the further expanded shape in which at least a part of the device is outside of the atrium, and
    expansion of the device from the expanded delivered shape to the further expanded shape said atrium into islets of atrial wall tissue separated by scar tissue that is unable to conduct electrical signals.

8. The device according to claim 1, wherein the device comprises a resorbable shape memory polymer configured for achieving said change of shape from said temporary delivery shape to said expanded delivered shape.

9. The device according to claim 8, wherein a time for resorption of the polymer is determinable by means of x-ray radiation, ultrasound, electron beams, or light of a defined wavelength.

10. The device according to claim 1, wherein the second segment is configured to fit in a branch of a pulmonary vein system having a smaller diameter than the first segment.

11. The device according to claim 1, wherein the at least one cutting arm has a form comprising at least one closed loop.

12. The device according to claim 1, wherein said body vessel into which the device is structured and arranged to be inserted is the coronary sinus.

13. The device according to claim 1, wherein an outside surface of the device is provided with drugs and wherein said drugs are selected from the group consisting of a drug adapted to increase a cutting effect through tissue, a drug adapted to prohibit a thickening of a wall of the body vessel in which the device is inserted, an antiarrhythmic drug, and combinations thereof.

14. The device according to claim 1, wherein an outside surface of the device is provided with a drug selected from the group consisting of an alcohol, glutaraldehyde, formaldehyde, a proteolytic enzyme, a collagenase, cyclosporin, taxiferol, rapamycin, tacrolimus, Endothelium Growth Factor, Heparin, amiodarone, sotalol, an antiarrhythmic drug, and combinations thereof.

15. The device according to claim 1, wherein said device has a net-like shape formed of closed loops.

16. A kit of shape-changing cutting devices according to claim 1, said kit comprising:
    a plurality of devices according to claim 1 wherein:
    at least one of the shape-changing devices is adapted to be inserted to a desired position at the orifice of a pulmonary vein in the heart,
    at least one of the shape-changing devices is adapted to be inserted to a desired position in the coronary sinus, and the kit is assembled from devices designed to fit to anatomical conditions of the treatment locations.

17. The kit according to claim 16, wherein one of the shape-changing devices is adapted to be inserted into the pulmonary vein and comprises an arm which, in the expanded delivered shape and/or further expanded shape, is arranged to contact another shape-changing device in the coronary sinus.

18. The kit according to claim 17, wherein said arm comprises a trough in an area to come in contact with a shape-changing device in the coronary sinus.

19. The kit according to claim 16, wherein at least one of the shape-changing devices is adapted to be inserted into the inferior vena cava or the superior vena cava.

20. The kit according to claim 16, wherein the kit comprises four shape-changing devices, each being adapted to be inserted into a respective pulmonary vein.

21. The kit according to claim 20, wherein at least one of the shape-changing devices is adapted to be inserted into a pulmonary vein comprises an arm which, in one or both of the expanded delivered shape and further expanded shape, is arranged to contact the shape-changing device in another pulmonary vein.

22. The kit according to claim 16, wherein at least one of the shape-changing devices is adapted to be inserted into the left atrial appendage or the right atrial appendage.

23. The kit according to claim 22, wherein the shape-changing device is adapted to be inserted into the left atrial appendage and wherein:
   said shape-changing device comprises an arm which, in one or both of the expanded delivered shape and further expanded shape, is arranged to contact the shape-changing device in a pulmonary vein and/or
   said shape-changing device comprises a film, which covers an end of the tubular shape of the device.

24. A kit of shape-changing cutting devices according to claim 1, said kit comprising a plurality of tissue cutting devices configured to reduce undesired signal transmission in a heart tissue in order to treat arrhythmia, wherein:
   each tissue cutting device is structured and arranged to be inserted in a temporary delivery shape through the vascular system and at least partly be positioned into said atrium that is intended to be treated and to be subsequently subjected to a change of shape, from said temporary delivery shape via an expanded delivered shape to a further expanded shape, extending at least beyond an outer surface of said atrial tissue,
   each tissue cutting device is configured to create cutting action for cutting of said
   heart tissue including said atrium, and wherein each tissue cutting device is structured and arranged to penetrate a wall of said heart tissue by said cutting action, in such a manner that a cut of said tissue created by said cutting action is continuously replaced by scar tissue that does not conduct electrical signals to isolate ectopic sites of said heart tissue causing said arrhythmia,
   at least one of the shape-changing devices is adapted to be inserted to a desired position at the orifice of a pulmonary vein in the heart,
   at least one of the shape-changing devices is adapted to be inserted to a desired position in the coronary sinus,
   the kit is assembled from devices designed to fit to anatomical conditions of the treatment locations, and
   wherein the said plurality of devices are configured to produce a cutting pattern that is substantially a Maze III-pattern, said cutting pattern comprising a plurality of cuts chosen from:
   a first cut around the left superior pulmonary vein (LSPV) and the left inferior pulmonary vein (LIPV) and a corresponding second cut around the right superior pulmonary vein (RSPV) and the right inferior pulmonary vein (RSPV);
   a third cut connecting the first cut and the second cut around the pulmonary veins (PV);
   a fourth cut from the third cut to the coronary sinus (CS);
   a fifth cut from the left pulmonary veins to the left atrial appendage;
   a sixth cut from the inferior vena cava (IVC) to the superior vena cava (SVC);
   a seventh cut connecting the second cut around the right pulmonary veins and the sixth cut between the IVC and the SVC;
   an eighth cut from the sixth cut between the IVC and the SVC along the right lateral atrium wall; and
   a ninth cut isolating the right atrial appendage.

* * * * *